United States Patent
Amako et al.

(10) Patent No.: US 6,417,309 B2
(45) Date of Patent: Jul. 9, 2002

(54) CURABLE ORGANOSILOXANE COMPOSITION

(75) Inventors: Masaaki Amako; Tadashi Okawa, both of Chiba Prefecture (JP)

(73) Assignee: Dow Corning Toray Silicone Co., Ltd., Tokyo (JP)

( * ) Notice: Subject to any disclaimer, the term of this patent is extended or adjusted under 35 U.S.C. 154(b) by 0 days.

(21) Appl. No.: 09/808,789

(22) Filed: Mar. 15, 2001

Related U.S. Application Data

(62) Division of application No. 09/409,810, filed on Sep. 30, 1999, now Pat. No. 6,252,029.

(30) Foreign Application Priority Data

| Sep. 30, 1998 | (JP) | 10-278538 |
| Sep. 30, 1998 | (JP) | 10-294580 |
| Mar. 31, 1999 | (JP) | 11-090575 |
| Jun. 17, 1999 | (JP) | 11-171113 |

(51) Int. Cl.⁷ .............................................. C08G 77/08
(52) U.S. Cl. ............................. 528/25; 528/15; 528/31; 528/32; 525/478; 524/862
(58) Field of Search ..................... 528/15, 25, 31, 528/32; 525/478; 524/862

(56) References Cited

U.S. PATENT DOCUMENTS

| 3,328,450 A | | 6/1967 | Plueddemann | 260/448.8 |
| 3,931,267 A | | 1/1976 | Brode | 260/448.8 R |
| 5,138,012 A | * | 8/1992 | Riding et al. | 525/478 |
| 5,204,438 A | | 4/1993 | Snow et al. | 528/25 |
| 5,266,663 A | | 11/1993 | Haus et al. | 526/110 |
| 5,726,271 A | | 3/1998 | Furukawa et al. | 528/29 |
| 6,252,029 B1 | * | 6/2001 | Amako et al. | 528/25 |

* cited by examiner

*Primary Examiner*—Margaret G. Moore
(74) *Attorney, Agent, or Firm*—Larry A. Milco; Catherine U. Brown

(57) ABSTRACT

A curable organosiloxane composition comprising: (A) an organopolysiloxane having at least two silicon atom-bonded alkenyl groups per molecule; (B) an organopolysiloxane having at least two silicon atom-bonded hydrogen atoms per molecule; (C) a compound having an alkenyl group and a phenol residue of the formula:

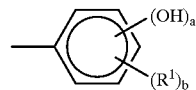

where $R^1$ is an alkyl group or alkoxy group, a is 1 or 2, and b is an integer from 0 to 3; and (D) a hydrosilylation reaction catalyst.

15 Claims, 6 Drawing Sheets

CURABLE ORGANOSILOXANE COMPOSITION

CROSS-REFERENCE TO RELATED APPLICATIONS

The present application is a division of application Ser. Nos. 09/409,810 filed Sep. 30, 1999, entitled "Hydroxyphenyl Group-Containing Organosilicon Compound, and Method for Manufacturing Same.", now U.S. Pat. No. 6,252,029 issued Jun. 26, 2001.

FIELD OF THE INVENTION

The present invention relates to a novel organosilicon compound containing hydroxyphenyl groups and aliphatic unsaturated bonds within the same molecules, and to a method for manufacturing this compound.

The present invention also relates to a curable organosiloxane composition, and more particularly relates to a curable organosiloxane composition which can be cured through a hydrosilylation reaction to form a cured product which will adhere well to a variety of thermosetting organic resins.

BACKGROUND OF THE INVENTION

Silicone compounds whose main components are an alkenyl group-containing organosiloxane and an organohydrogenpolysiloxane and which cure in the presence of a platinum-based catalyst are called addition reaction-curing silicone compositions, and are used in many different fields of industry. However, when this type of silicone composition cures, the surface thereof becomes inert, which makes it extremely difficult to bond an epoxy resin, phenol resin, or any of various other organic resins to this cured material. Various attempts have therefore been made at bonding these materials together, such as subjecting the surface of a cured product of an addition reaction-curing silicone composition to an ozone treatment, then bringing one of various organic resins into contact with this ozone-treated surface and curing it. This method, however, is not satisfactory for practical purposes because of its drawback in that adhesion decreases over time. Accordingly, there is a need for an adhesion imparter for bonding various organic resins to the cured product of an addition reaction-curing silicone composition. It is believed that an organosilicon compound containing hydroxyphenyl groups (as functional groups for enhancing adhesion with an organic resin) and alkenyl groups (as functional groups incorporated into the addition reaction cured product) in the same molecules would be effective as this adhesion imparter.

DETAILED DESCRIPTION OF THE INVENTION

Figure 1:
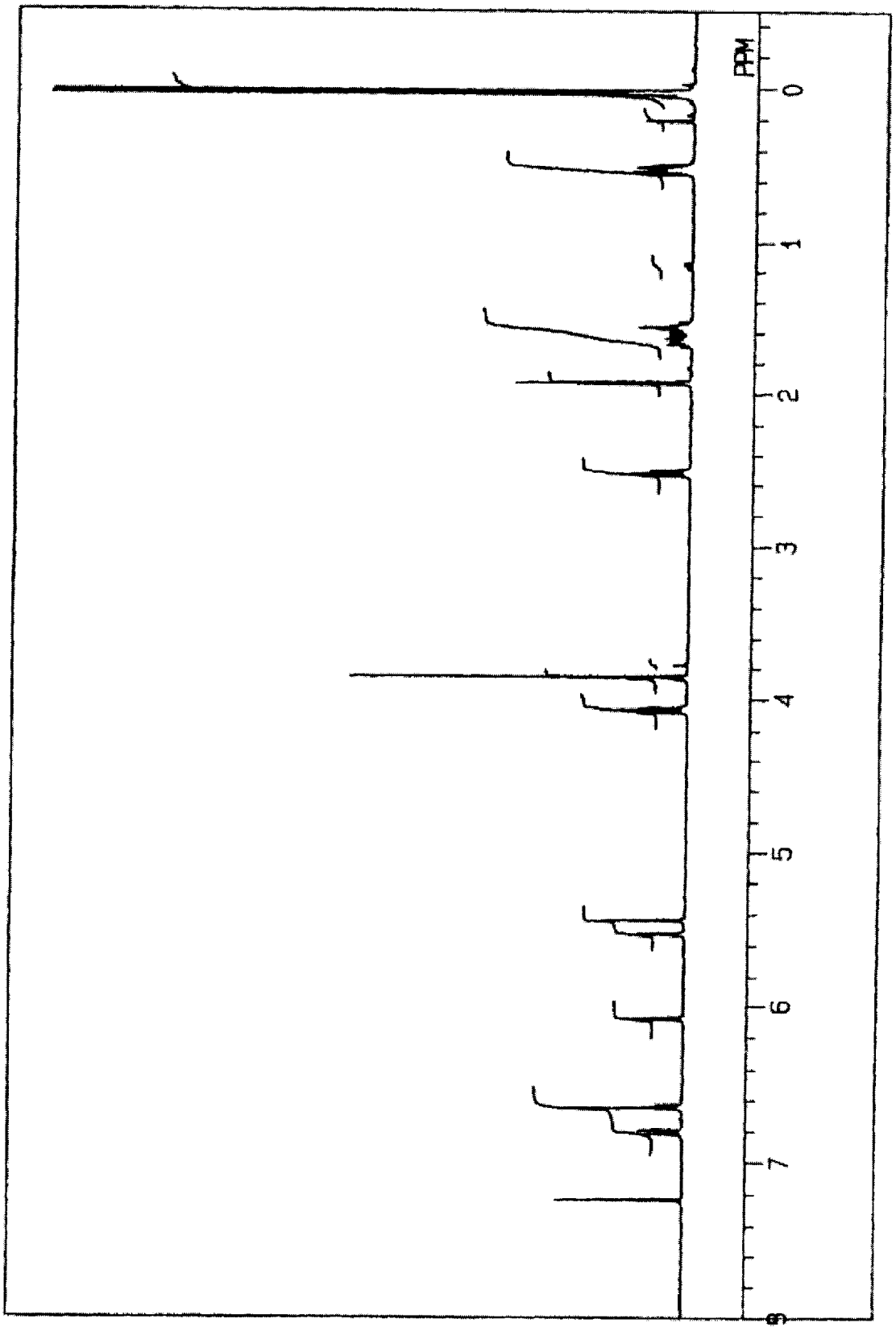
FIG. 1 is a nuclear magnetic resonance analysis chart of the hydroxyphenyl group-containing methacrylic functional organosilicon compound synthesized in Working Example 1.
Figure 2:
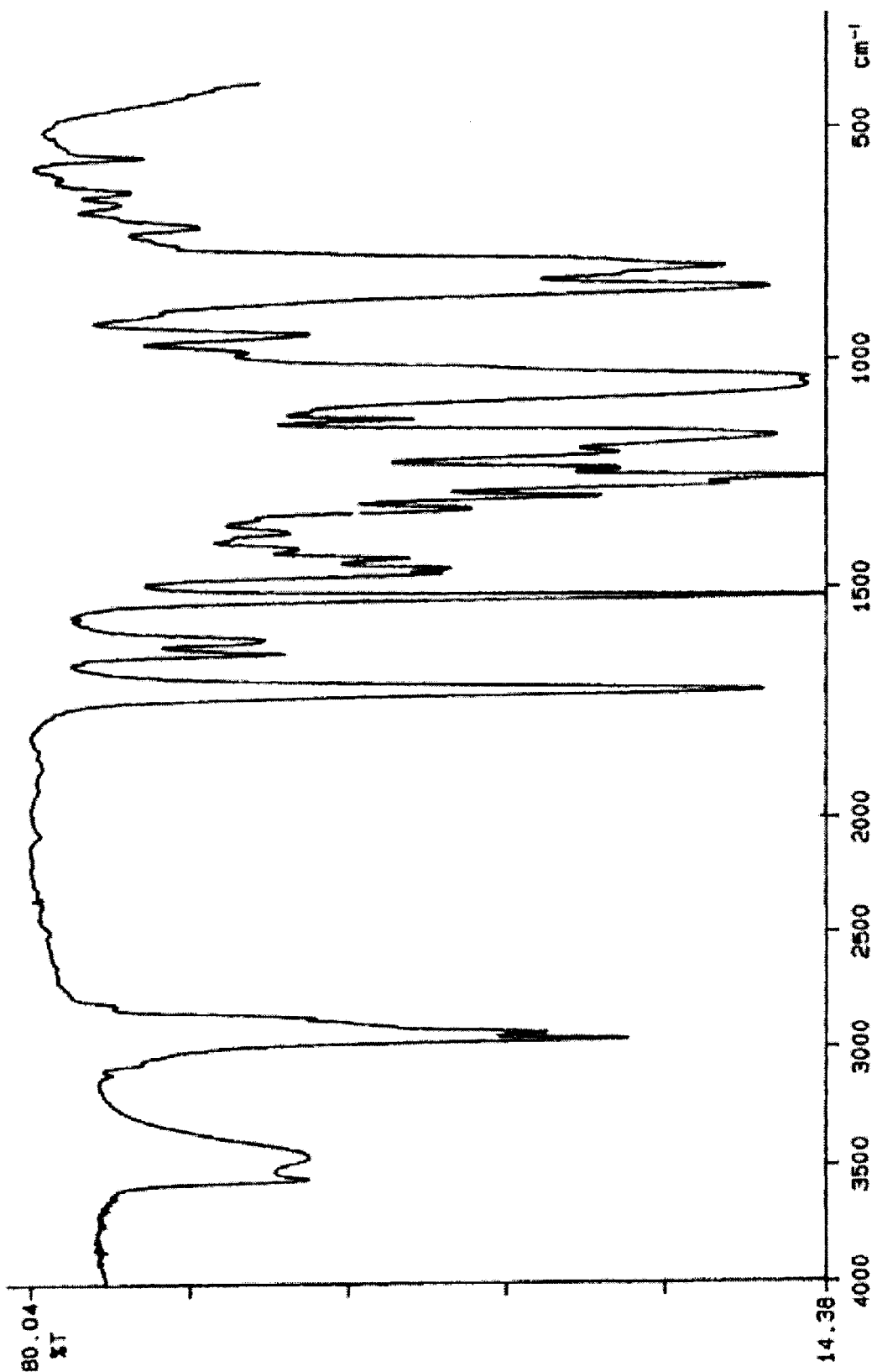
FIG. 2 is an infrared spectroscopic analysis chart of the hydroxphenyl group-containing methacrylic functional organosilicon compound synthesized in Working Example 1.
Figure 3:
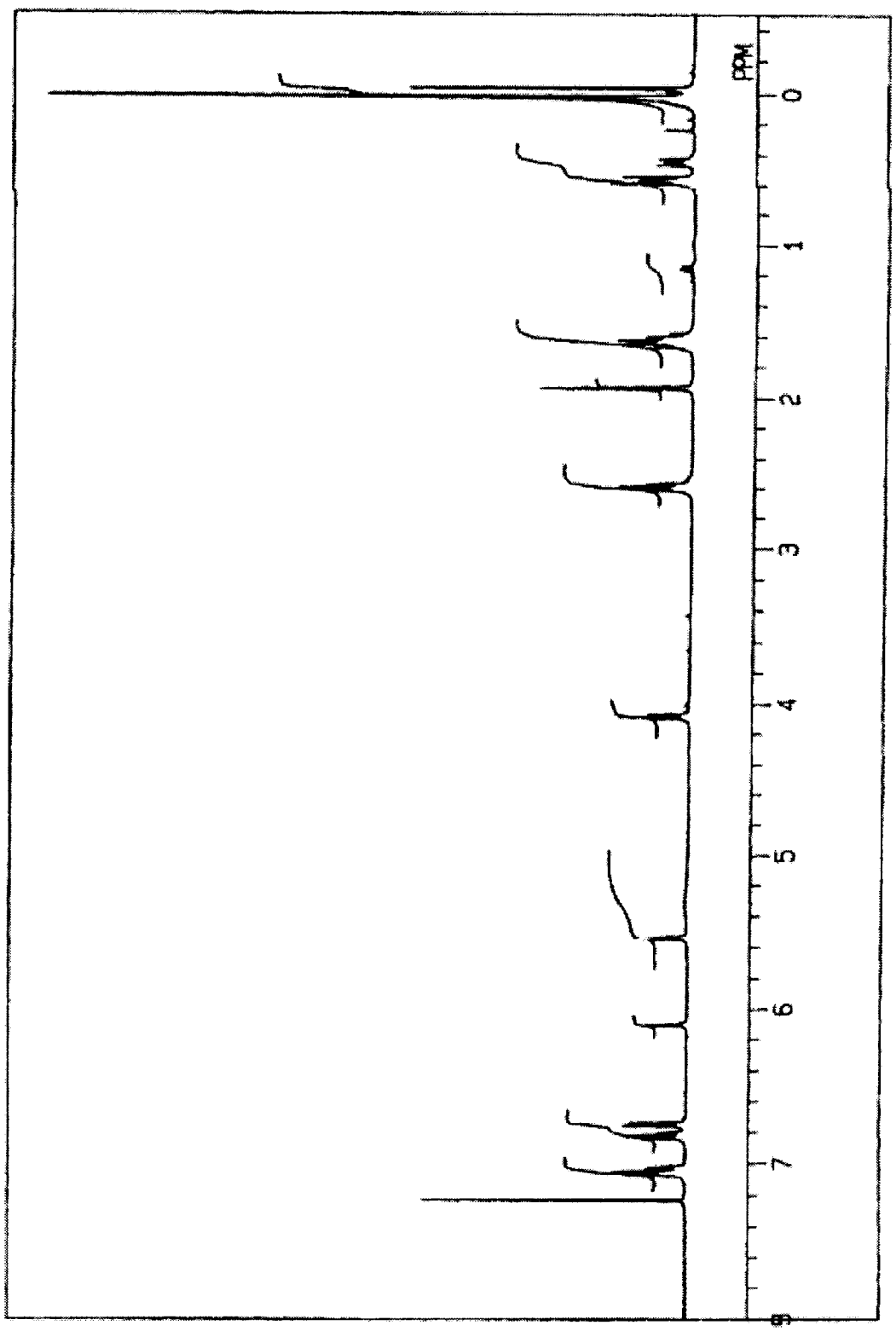
FIG. 3 is a nuclear magnetic resonance analysis chart of the hydroxphenyl group-containing methacrylic functional organosilicon compound synthesized in Working Example 2.
Figure 4:
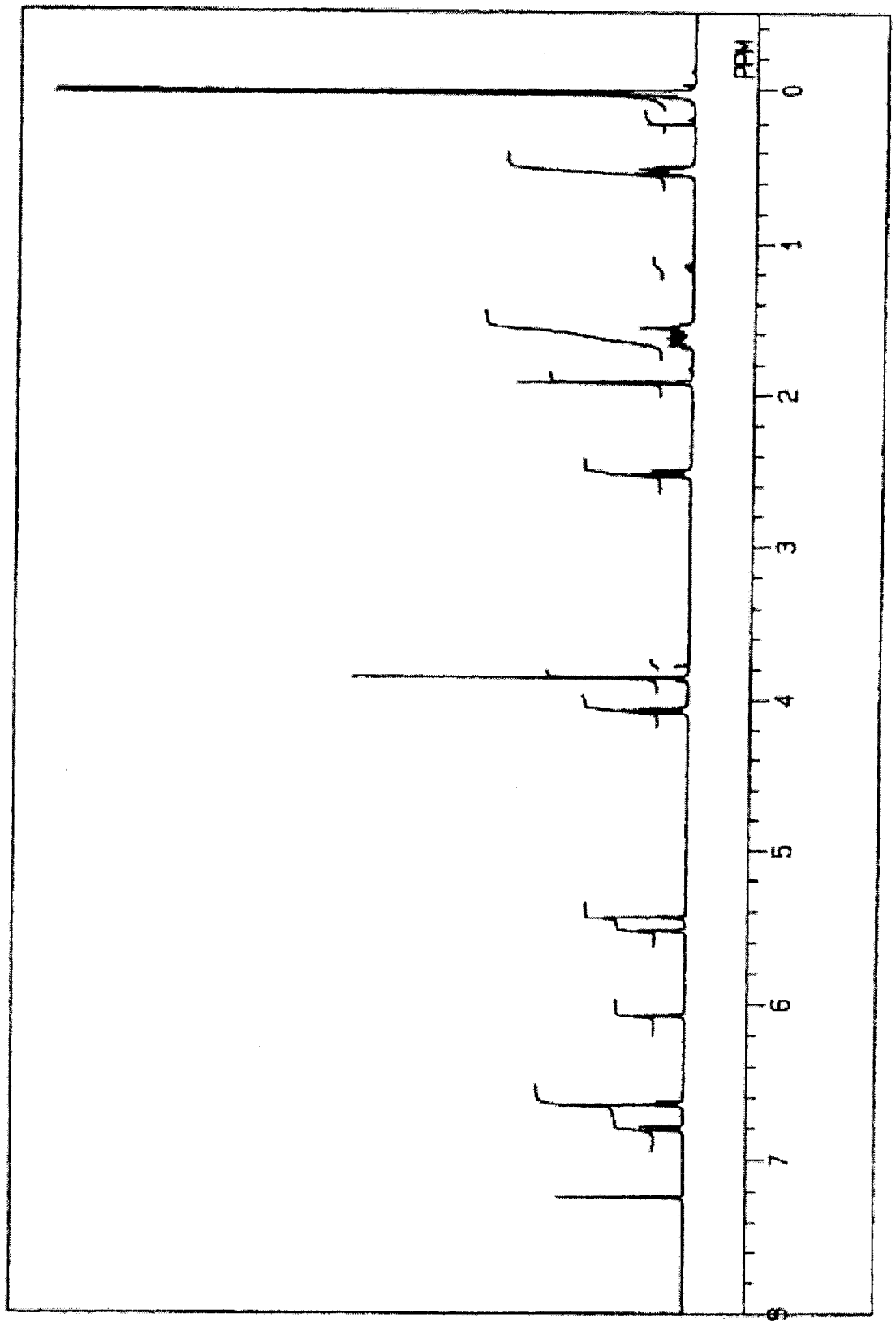
FIG. 4 is an infrared spectroscopic analysis chart of the hydroxyphenyl group-containing methacrylic functional organosilicon compound synthesized in Working Example 2.
Figure 5:
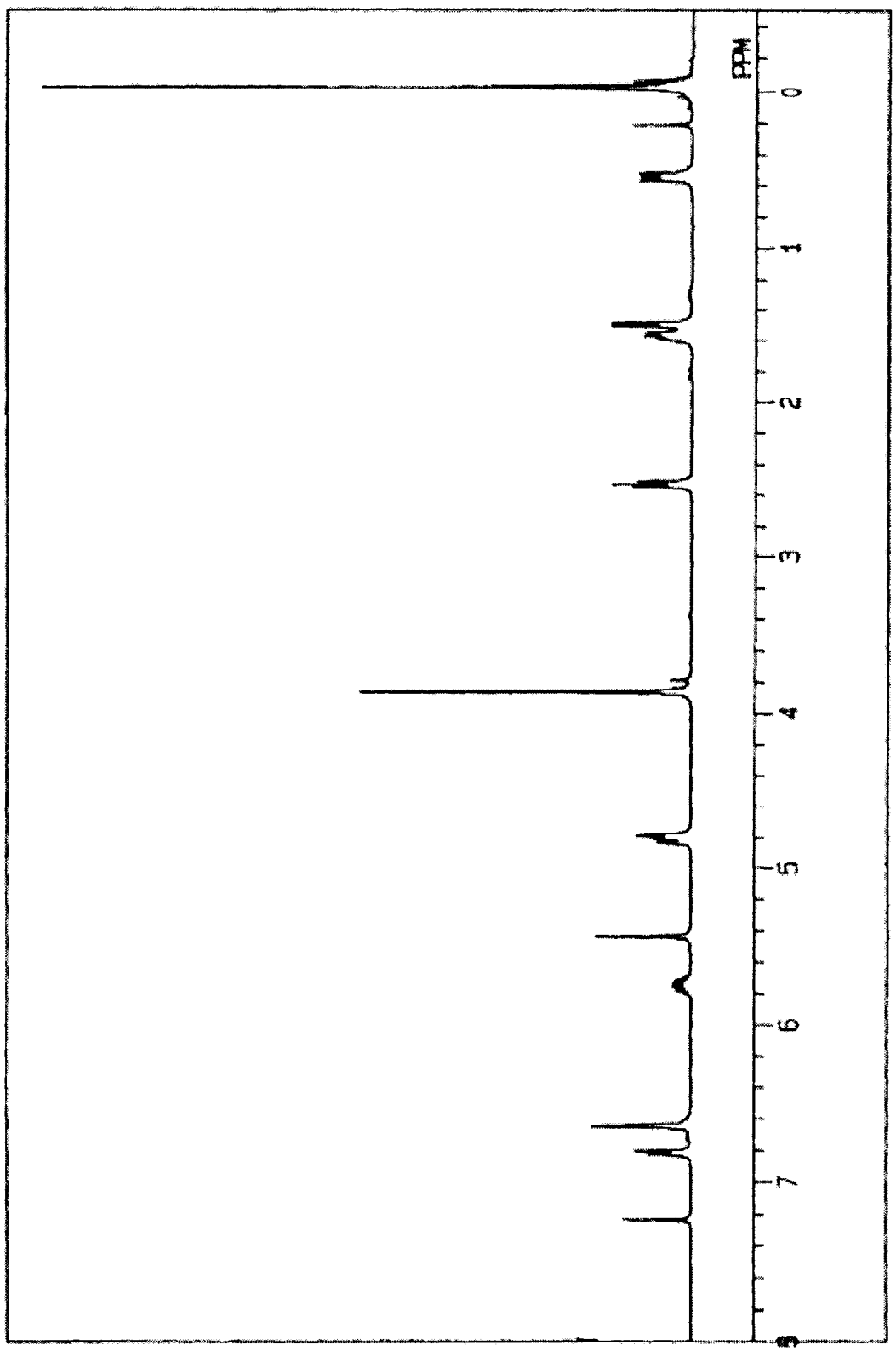
FIG. 5 is a nuclear magnetic resonance analysis chart of the hydroxyphenyl group-containing methacrylic functional organosilicon compound synthesized in Working Example 3.
Figure 6:
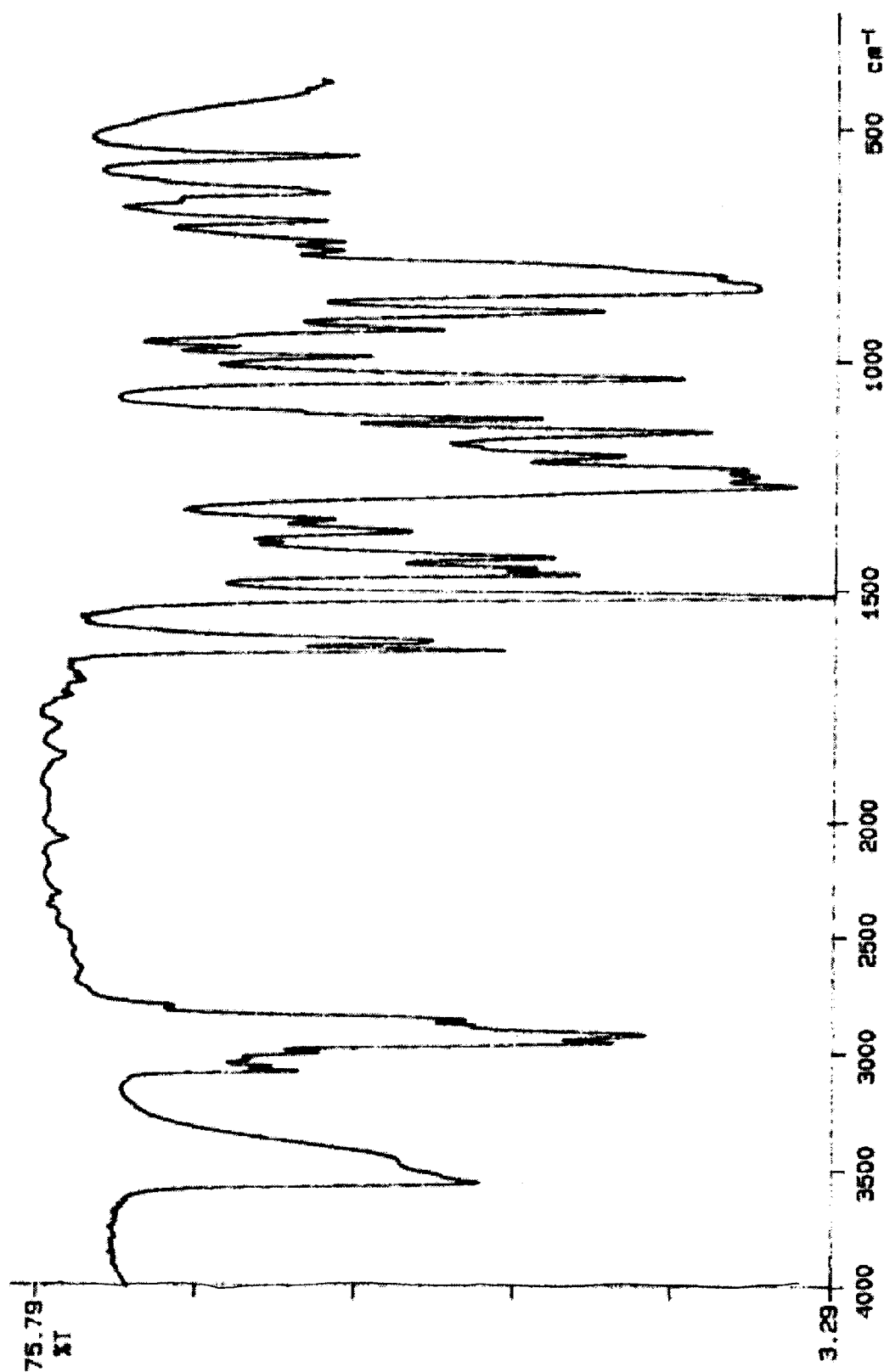
FIG. 6 is an infrared spectroscopic analysis chart of the hydroxyphenyl group-containing methacrylic functional organosilicon compound synthesized in Working Example 3.

The present invention relates to a hydroxyphenyl group-containing organosilicon compound expressed by the general formula:

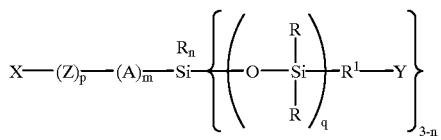

where X is an alkenyl group; Z is a phenylene group or a carbonyloxy group expressed by —C(O)O—; Y is a substituted or unsubstituted hydroxyphenyl group; $R^1$ is a hydrocarbon group with two or more carbon atoms, with the various groups being the same or different; R is a monovalent hydrocarbon group containing no aliphatic unsaturated bonds, with the various groups being the same or different; A is a divalent hydrocarbon group with one or more carbon atoms or a group expressed by the formula —$R^2$—O—$R^2$— (where $R^2$ is a divalent hydrocarbon group); m and p are each independently 0 or 1; n is a number from 0 to 2; and q is an integer from 0 to 7, and to a method for manufacturing this compound.

The hydroxyphenyl group-containing organosilicon compound of the present invention is a compound expressed by the general formula given above, containing hydroxyphenyl groups and aliphatic unsaturated bond-containing monovalent hydrocarbon groups in its molecules. In the above formula, X is an alkenyl group, examples of which include the vinyl group, allyl group, isopropenyl group, and hexenyl group. Z is a phenylene group or a carbonyloxy group expressed by —C(O)O—. Examples of phenylene groups include the o-phenylene group, m-phenylene group, and p-phenylene group. Y is a substituted or unsubstituted hydroxyphenyl group, examples of which include an alkyl group-substituted hydroxyphenyl group and an alkoxy group-substituted hydroxyphenyl group. There are no particular restrictions on the substitution position of the alkyl group or alkoxy group. Examples of the alkyl group include the methyl group, ethyl group, propyl group, and butyl group, and examples of the alkoxy group include the methoxy group, ethoxy group, propoxy group, and butoxy group. Examples of substituted or unsubstituted hydroxyphenyl groups include the 2-hydroxyphenyl group, 4-hydroxyphenyl group, 3,4-dihydroxyphenyl group, 3,5-dihydroxyphenyl group, and other such hydroxyphenyl groups; the 3,5-di-tert-butyl-4-hydroxyphenyl group, 3-methyl-4-hydroxyphenyl group, and other such alkyl group-substituted hydroxyphenyl groups; and the 4-hydroxy-3-methoxyphenyl group, 3,5-dimethoxy-4-hydroxyphenyl group, and other such alkoxy group-substituted hydroxyphenyl groups, but in terms of ready availability it is preferable for Y to be the 2-hydroxyphenyl group or 4-hydroxy-3-methoxyphenyl group. $R^1$ is a hydrocarbon group with two or more carbon atoms, with the various groups being the same or different, examples of which include the ethylene group, propylene group, butylene group, hexylene group, and other such alkylene groups, and the phenylene group and other such arylene groups. R is a monovalent hydrocarbon group containing no aliphatic unsaturated bonds, with the various groups being the same or different, examples of which include the methyl group, ethyl group, butyl group, pentyl group, hexyl group, and other such alkyl groups; the phenyl group, tolyl group, xylyl group, and other such aryl group; and the benzyl group, phenethyl group, and other such aralkyl groups. A is a divalent hydrocarbon group with one or more carbon atoms or a group expressed by the formula —$R^2$—O—$R^2$— (where $R^2$ is a divalent hydrocarbon group; examples include the alkylene groups and arylene groups listed above), examples of which include the ethylene group, propylene group, butylene group, hexylene group, and an ethyleneoxypropylene group. m and p are each independently 0 or 1. n is a number from 0 to 2, and q is an integer from 0 to 7.

The compounds listed below are examples of the hydroxyphenyl group-containing organosilicon compound of the present invention.

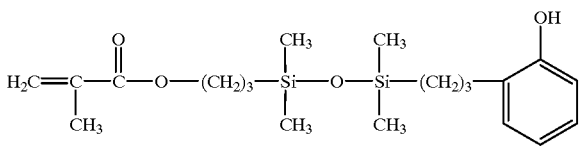

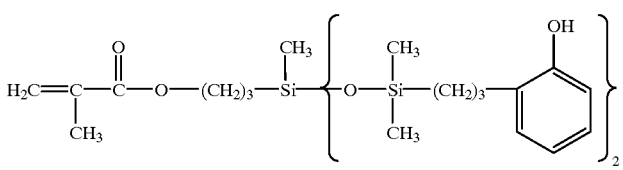

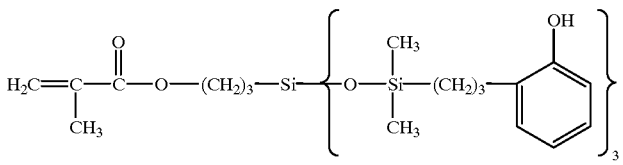

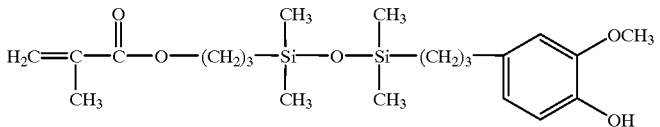

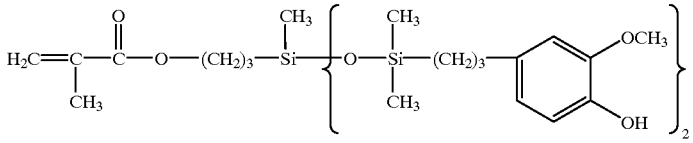

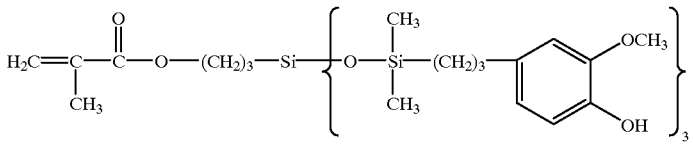

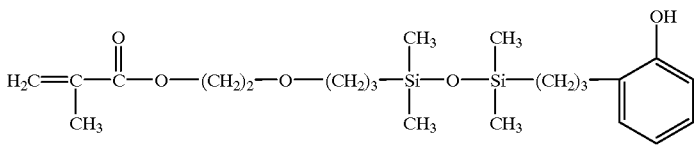

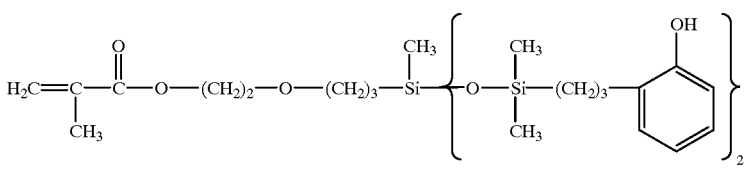

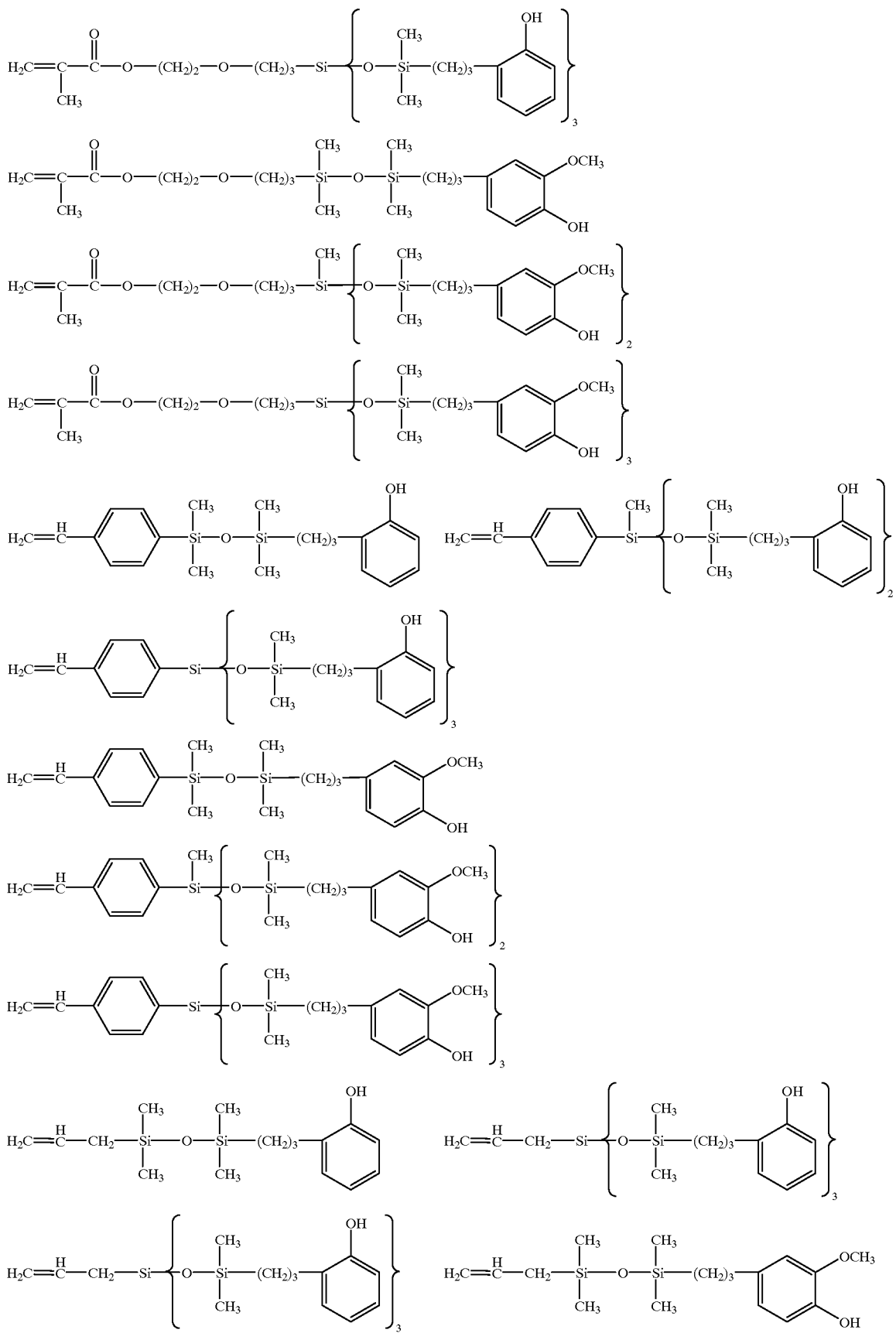

-continued
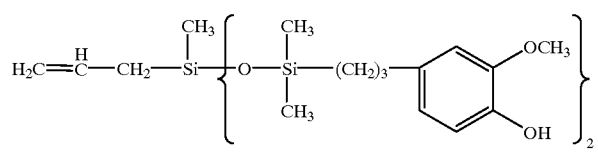
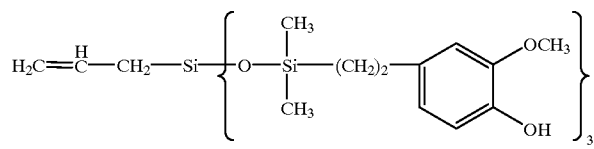
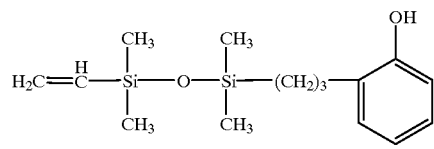
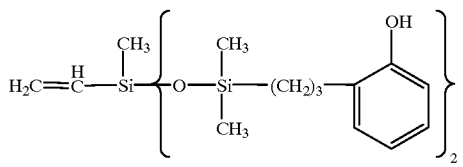
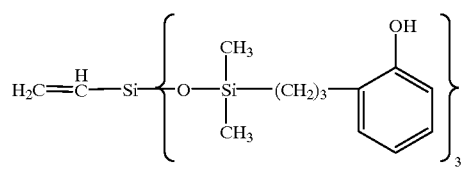
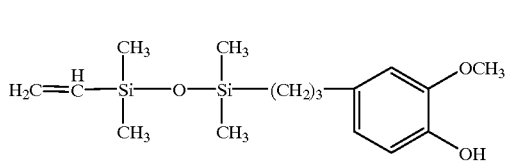
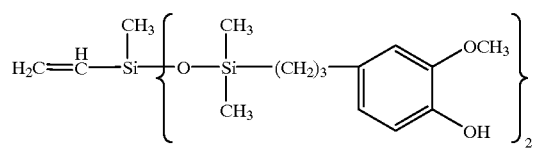
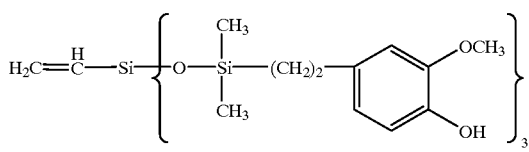
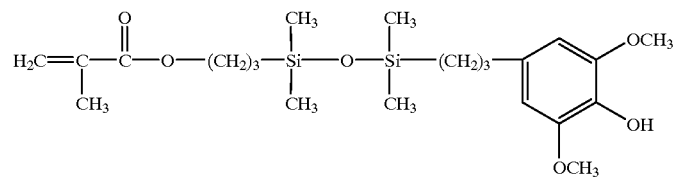
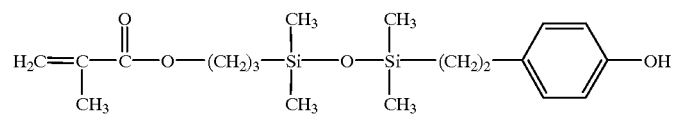
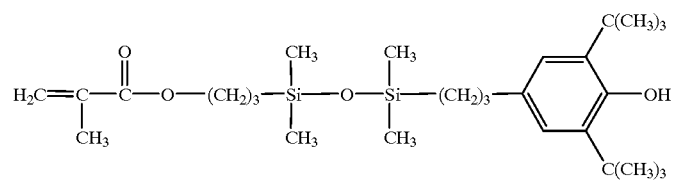
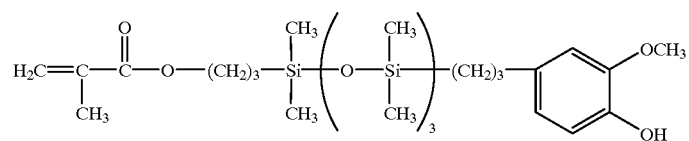
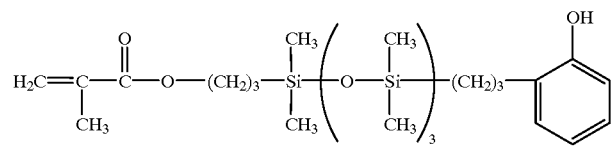

-continued

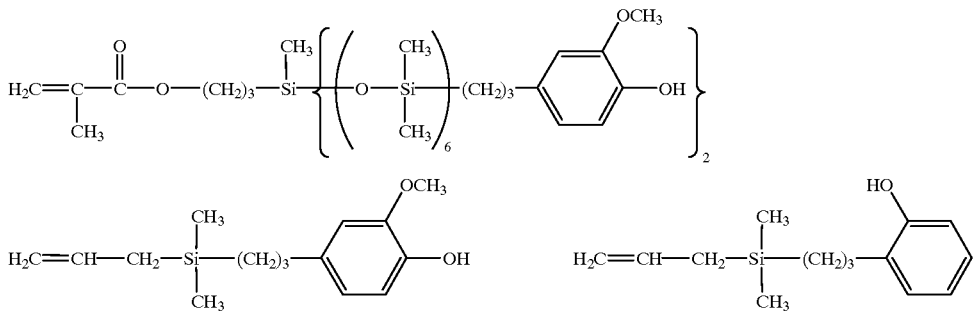

The method for manufacturing the hydroxyphenyl group-containing organosilicon compound of the present invention will also be described herein.

The hydroxphenyl group-containing organosilicon compound manufacturing method of the present invention is a method for manufacturing a hydroxphenyl group-containing organosilicon compound comprising reacting:

(A) a silicon atom-bonded hydrogen atom-containing organosilicon compound expressed by the general formula:

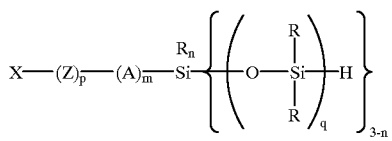

where X is an alkenyl group; Z is a phenylene group or a carbonyloxy group expressed by —C(O)O—; R is a monovalent hydrocarbon group containing no aliphatic unsaturated bonds, with the various groups being the same or different; A is a divalent hydrocarbon group with one or more carbon atoms or a group expressed by the formula —$R^2$—O—$R^2$— where $R^2$ is a divalent hydrocarbon group; m and p are 0 or 1; n is a number from 0 to 2; and q is an integer from 0 to 7 and (B) an aliphatic unsaturated bond-containing compound expressed by the general formula:

$$R^3—Y^1$$

where $R^3$ is an aliphatic unsaturated bond-containing monovalent hydrocarbon group, and $Y^1$ is a substituted or unsubstituted hydroxyphenyl group in the presence of a hydrosilylation catalyst.

Another method for manufacturing a hydroxyphenyl group-containing organosilicon compound comprises (I) reacting:

(A) a silicon atom-bonded hydrogen atom-containing organosilicon compound expressed by the general formula:

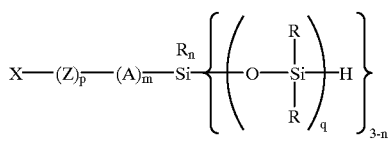

where X is an alkenyl group; Z is a phenylene group or a carbonyloxy group expressed by —C(O)O—; R is a monovalent hydrocarbon group containing no aliphatic unsaturated bonds, with the various groups being the same or different; A is a divalent hydrocarbon group with one or more carbon atoms or a group expressed by the formula —$R^2$—O—$R^2$— where R is a divalent hydrocarbon group; m and p are 0 or 1; n is a number from 0 to 2; and q is an integer from 0 to 7 and (B) an aliphatic unsaturated bond-containing compound expressed by the general formula:

$$R^3—Y^2$$

where $R^3$ is an aliphatic unsaturated bond-containing monovalent hydrocarbon group, and $Y^2$ is a triorganosiloxified substituted or unsubstituted hydroxyphenyl group in the presence of a hydrosilylation catalyst, and (II) desilylating the product of (I).

In the above-noted methods, the silicon atom-bonded hydrogen atom-containing organosilicon compound of component (A) is such that X, Z, A, R, n, m, and p in the above formulas are the same as given above. These organosilicon compounds can be manufactured by a conventional method. For instance, it is known that a silicon atom-bonded hydrogen atom-containing organosilicon compound expressed by the formula $CH_2$=$C(CH_3)COO(CH_2)_3Si\{OSi(CH_3)_2H\}_3$ can be produced by the dropwise addition of a silane expressed by the formula $H(CH_3)_2SiCl$ to a silane expressed by the formula $CH_2$=$C(CH_3)COO(CH_2)_3Si(OCH_3)_3$ in the presence of a mixed solvent comprising water and ether (see U.S. Pat. No. 3,398,017). This compound can also be manufactured by subjecting a methacrylic functional group containing chlorosilane to hydrolysis in the presence of 1,1,3,3-tetramethyldisiloxane, or subjecting a methacrylic functional group containing chlorosilane to hydrolysis to produce silanol, and then subjecting this product to a reaction with a diorganochlorosilane. Here, it is preferable to use triethylamine, pyridine, or another such amine as a scavenger for the hydrogen chloride that is produced so as to suppress the condensation of the silanol groups. The above compound can also be synthesized by allowing 1,1,3,3-tetramethyldisiloxane to react with a silane expressed by the formula $(CH_2$=$C(CH_3)COO(CH_2)_3Si(OCH_3)_3$ in the presence of a strong acid and a carboxylic acid.

In the aliphatic unsaturated bond-containing phenol compound of component (B), $R^3$ in the above formula is an aliphatic unsaturated bond-containing monovalent hydrocarbon group, examples of which include the vinyl group, allyl group, isopropenyl group, and hexenyl group. Of these, an allyl group is preferred. $Y^1$ is a substituted or unsubstituted hydroxyphenyl group. Examples of $Y^1$ are the same hydroxyphenyl groups listed as examples for Y above. $Y^2$ is a triorganosiloxified substituted or unsubstituted hydroxyphenyl group. Examples of this organic group include groups in which the hydroxyl groups of the hydroxyphenyl groups listed as examples of Y above have been trimethylsiloxified. It is particularly favorable for component (B) to be 2-allylphenol, eugenol, or a trimethylsilyl ether of these. Because phenolic hydroxyl groups undergo a dehydration condensation reaction with silicon atom-bonded hydrogen atoms in the presence of a hydrosilylation reaction catalyst, when a product of particularly high purity is required, it is preferable for component (B) to be an aliphatic unsaturated bond-containing compound in which the phenolic hydroxyl groups have been triorganosiloxified.

Examples of hydrosilylation catalysts include transition metal complex catalysts from Group 8 of the Periodic Table. Of these, a platinum-based catalyst is particularly effective. Such favorable catalysts include chloroplatinic acid and alcohol solutions thereof, olefin complexes of platinum, complexes of platinum and a vinyl group-containing siloxane, and other such platinum compounds.

A method in which component (B) and the hydrosilylation catalyst are pre-mixed, and component (A) is then slowly added dropwise to this mixture, is preferred in order to suppress the addition reaction velocity between the silicon atom-bonded hydrogen atoms and the alkenyl groups in component (A). The ratio between the amount of component (A) and the amount of component (B) is usually such that the ratio of the equivalents of aliphatic unsaturated bonds in component (B) with respect to the equivalents of silicon atom-bonded hydrogen atoms in component (B) is at least 0.8. A range of 0.8 to 2.00 is preferred, and a range of 0.9 to 1.5 is particularly preferred. This reaction can be conducted without a solvent, although it is preferable for it to be conducted in the presence of an organic solvent. Solvents that can be used include benzene, toluene, xylene, and other aromatics; pentane, hexane, heptane, octane, decane, and other aliphatics; tetrahydrofuran, diethyl ether, dibutyl ether, and other ethers; acetone, methyl ethyl ketone, and other ketones; ethyl acetate, butyl acetate, and other esters; and carbon tetrachloride, trichloroethane, dichloromethylene, chloroform, and other chlorinated hydrocarbons. The reaction can be conducted at room temperature, but it is usually preferable for it to be conducted at a temperature between 50 and 200° C. The reaction solution can be analyzed during the reaction by gas chromatography analysis (GLC) or infrared spectroscopic analysis (IR), and the reaction is considered to be concluded at the point when the characteristic absorption of the silicon atom-bonded hydrogen atom-containing organosiloxane in component (A) disappears. Upon conclusion of the reaction, the aliphatic unsaturated bond- and hydroxyphenyl group-containing organosilicon compound of the present invention is obtained by removing any unreacted component (B) or low-boiling matter such as an organic solvent by distillation under heating and reduced pressure.

When an aliphatic unsaturated bond compound in which the phenolic hydroxyl groups have been triorganosiloxified is used as component (B), an adduct in which the phenolic hydroxyl groups have been triorganosiloxified will be obtained, and therefore these triorganosilyl groups shall be removed and the hydroxyphenyl groups regenerated. A conventional method can be used for this desilylation, but a preferable method is one in which a triorganosiloxified adduct is desilylated in the presence of a protic solvent using an amine compound or ammonia as a catalyst; with this method, there are no side reactions, and the targeted hydroxyphenyl group-containing organosilicon compound is obtained at a high yield.

Because this hydroxyphenyl group-containing organosilicon compound of the present invention contains an aliphatic unsaturated bond-containing monovalent hydrocarbon group in each molecule, it is miscible in addition reaction-curing silicone compositions, and will cure upon reaction with the organohydrogenpolysiloxanes in these addition reaction-curing silicone compositions. Also, because it contains hydroxyphenyl groups in its molecules, the cured product of an addition reaction-curing silicone composition that contains this organosilicon compound will become a cured silicone having hydroxyphenyl groups on its surface, and will have the characteristic of adhering to epoxy resins, phenol resins, and various other organic resins. Therefore, the hydroxyphenyl group-containing organosilicon compound of the present invention is useful as an adhesion imparter in applications where this characteristic is needed, such as the bonding of addition reaction-curing silicone compositions to various substrates.

This invention further relates to a curable organosiloxane composition comprising:

(A) an organopolysiloxane having at least two silicon atom-bonded alkenyl groups per molecule;

(B) an organopolysiloxane having at least two silicon atom-bonded hydrogen atoms per molecule;

(C) a compound having an alkenyl group and a phenol residue expressed by the general formula:

where $R^1$ is an alkyl group or alkoxy group, a is 1 or 2, and b is an integer from 0 to 3 in an amount of 0.1 to 50 weight parts per 100 weight parts of component (A); and (D) a hydrosilylation reaction catalyst.

Component (A) is an organopolysiloxane having at least two silicon atom-bonded alkenyl groups per molecule. Examples of the molecular structure of component (A) include linear, linear with some branches, branched, cyclic, and reticulated, but linear or branched is preferred for the purpose of the cured product of this composition exhibiting an elastomeric form such as a gel. There are no restrictions on the viscosity of component (A), and component (A) can be anything from a low-viscosity organopolysiloxane oligomer to a high-viscosity organopolysiloxane raw rubber. However, a viscosity at 25° C. within the range of 100 to 1,000,000 mm²/s is preferred because this composition will be easier to prepare and to handle. Examples of the silicon atom-bonded alkenyl groups in component (A) include the vinyl group, allyl group, isopropenyl group, butenyl group, pentenyl group, hexenyl group, heptenyl group, octenyl group, nonenyl group, and decenyl group, with the vinyl group being particularly preferred. Enhanced hydrosilylation reactivity will be exhibited if the carbon-carbon double bonds in these alkenyl groups are located at the terminals on the opposite end from the silicon atoms to which the alkenyl groups are bonded. Examples of groups that can be bonded to the silicon atoms besides the alkenyl groups in component (A) include the methyl group, ethyl group, propyl group, butyl group, pentyl group, hexyl group, and other such alkyl groups; the phenyl group, tolyl group, xylyl group, and other such aryl groups; the benzyl group, phenethyl group, and other such aralkyl groups; and other monovalent hydrocarbon groups having no aliphatic unsaturated bonds. Furthermore, a small amount of hydroxyl groups, alkoxy groups, haloalkyl groups, or the like may also be included. It is preferable for at least half of the groups bonded to the silicon atoms in component (A) to be methyl groups.

Examples of the organopolysiloxane of component (A) include a trimethylsiloxy-endblocked methylvinylpolysiloxane, a trimethylsiloxy-endblocked dimethylsiloxane-methylvinylsiloxane copolymer, a trimethylsiloxy-endblocked diphenylsiloxane-methylvinylsiloxane copolymer, a dimethylvinylsiloxy-endblocked dimethylpolysiloxane, a dimethylvinylsiloxy-endblocked dimethylsiloxane-methylvinylsiloxane copolymer, a dimethylvinylsiloxy-endblocked dimethylsiloxane-diphenylsiloxane copolymer, a cyclic methylvinylpolysiloxane, an organopolysiloxane comprising siloxane units expressed by the formula $SiO_{4/2}$ and siloxane units expressed by the formula $CH_2=CH(CH_3)_2SiO_{1/2}$, and an organopolysiloxane comprising siloxane units expressed by the formula $SiO_{4/2}$, siloxane units expressed by the formula $(CH_3)_3SiO_{1/2}$, and siloxane units expressed by the formula $CH_2=CH(CH_3)_2SiO_{1/2}$.

Component (B) is the curing agent of this composition, and is an organopolysiloxane having at least two silicon atom-bonded hydrogen atoms per molecule. Examples of the molecular structure of component (B) include linear, linear with some branches, branched, cyclic, reticulated, and star-shaped. There are no restrictions on the viscosity of component (B), and component (B) may vary from a low-viscosity organopolysiloxane oligomer to a high-viscosity organopolysiloxane raw rubber. However, a viscosity at 25° C. within the range of 1 to 100,000 mm²/s is preferred because this composition will be easier to handle. Examples of groups that can be bonded to the silicon atoms besides the hydrogen atoms in component (B) include the methyl group, ethyl group, propyl group, butyl group, pentyl group, hexyl group, and other such alkyl groups; the phenyl group, tolyl group, xylyl group, and other such aryl groups; the benzyl group, phenethyl group, and other such aralkyl groups; and other monovalent hydrocarbon groups having no aliphatic unsaturated bonds. Furthermore, to the extent that the object of the present invention is not compromised, a small amount of hydroxyl groups, alkoxy groups, haloalkyl groups, or the like may also be included. It is preferable for at least half of the groups bonded to the silicon atoms in component (B) to be methyl groups.

Examples of the organopolysiloxane of component (B) include a trimethylsiloxy-endblocked methylhydrogenpolysiloxane, a trimethylsiloxy-endblocked dimethylsiloxane-methylhydrogensiloxane copolymer, a trimethylsiloxy-endblocked diphenylsiloxane-methylhydrogensiloxane copolymer, a dimethylhydrogensiloxy-endblocked dimethylsiloxane-methylhydrogensiloxane copolymer, a cyclic methylhydrogenpolysiloxane, an organopolysiloxane comprising siloxane units expressed by the formula $SiO_{4/2}$ and siloxane units expressed by the formula $(CH_3)_2HSiO_{1/2}$, and an organopolysiloxane comprising siloxane units expressed by the formula $SiO_{4/2}$, siloxane units expressed by the formula $(CH_3)_3SiO_{1/2}$, and siloxane units expressed by the formula $(CH_3)_2HSiO_{1/2}$.

The amount of component (B) contained in this composition is an amount large enough to cure this composition; from 0.5 to 20 mol of silicon atom-bonded hydrogen atoms in this component per mole of total alkenyl groups in components (A) and (C). It is preferred that this amount be such that the range is from 0.5 to 10 mol, and more particularly, from 1.0 to 5 mol. Note that a composition will tend not to cure adequately if the content of component (B) is less than the lower end of the above range, but if the upper end of the above range is exceeded, the composition will tend to foam during curing, or the physical properties of the cured product that is obtained will tend to suffer.

Component (C) is a compound having an alkenyl group and a phenol residue expressed by the general formula:

This component serves to enhance the adhesion of a variety of thermosetting organic resins to the cured product obtained by curing this composition. Examples of the alkenyl group in component (C) include the vinyl group, allyl group, isopropenyl group, butenyl group, pentenyl group, hexenyl group, heptenyl group, octenyl group, nonenyl group, and decenyl group. In the phenol residue in component (C), $R^1$ in the formula is an alkyl group or alkoxy group. Examples of this alkyl group include the methyl group, ethyl group, n-propyl group, 1-propyl group, n-butyl group, 1-butyl group, and t-butyl group. Examples of this alkoxy include the methoxy group, ethoxy group, and propoxy group. Also, in the phenol residue in component (C), a in the formula is 1 or 2, and preferably 1, and b is an integer from 0 to 3, and preferably 0 to 2. Examples of this phenol residue include the 2-hydroxyphenyl group, 4-hydroxyphenyl group, 3,4-dihydroxyphenyl group, 3,5-dihydroxyphenyl group, 3,5-di-t-butyl-4-hydroxyphenyl group, 3-methyl-4-hydroxyphenyl group, 4-hydroxy-3-methoxyphenyl group, and 3,5-dimethoxy-4-hydroxyphenyl group. In terms of ready availability, the 2-hydroxyphenyl group and the 4-hydroxy-3-methoxyphenyl group are preferred.

Examples of the compound of component (C) include 2-allylphenol, eugenol, ortho-eugenol, 4-allyl-2,6-dimethoxyphenol, and other such alkenyl group-containing phenol compounds, and organosilicon compounds expressed by the general formula:

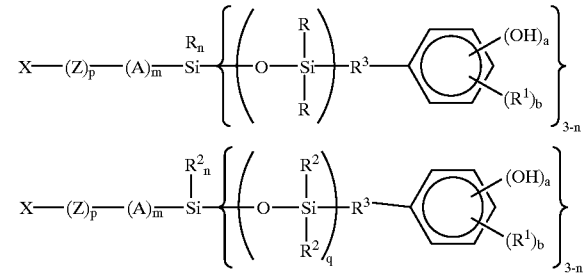

As to the organosilicon compound of component (C), X in the formula is an alkenyl group, examples of which include the vinyl group, allyl group, isopropenyl group, and butenyl group, with the allyl group and isopropenyl group being particularly preferred. Z in the formula is an oxy group expressed by the formula —O—, a carboxy group expressed by the formula —C(O)O—, or a phenylene group. Examples of this phenylene group include an o-phenylene group, m-phenylene group, and p-phenylene group. A in the formula is a divalent hydrocarbon group, a group expressed by the formula:

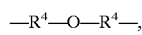

or a group expressed by the formula:

—$R^5$—O—.

Examples of the divalent hydrocarbon group of A include the methylene group, ethylene group, propylene group, and other such alkylene groups; and the methylenephenylene group, ethylenephenylene group, and other such alkylenearylene groups. The $R^4$ groups in the above formula are the same or different divalent hydrocarbon groups, examples of which include the methylene group, ethylene group, propylene group, and other such alkylene groups; and the methylenephenylene group, ethylenephenylene group, and other such alkylenearylene groups. $R^5$ in the above formula is a substituted or unsubstituted divalent hydrocarbon group, examples of which include the methylene group, ethylene group, propylene group, and other such alkylene groups, the methylenephenylene group, ethylenephenylene group, and other such alkylenearylene groups, and other unsubstituted divalent hydrocarbon groups, or the hydroxyethylene group, hydroxypropylene group, and other hydroxy group-substituted divalent hydrocarbon groups. It is preferable for this A to be an alkylene group, or a methyleneoxyethylene group, methyleneoxypropylene group, ethyleneoxypropylene group, propyleneoxypropylene group, or other such alkyleneoxyalkylene group, with an alkylene group being particularly preferred. $R^1$ in the formula is an alkyl group or alkoxy group, examples of which are the same as those listed above. The $R^2$ groups in the formula are the same or different monovalent hydrocarbon groups having no aliphatic unsaturated bonds, examples of which include the methyl group, ethyl group, propyl group, butyl group, pentyl group, hexyl group, and other such alkyl groups; the phenyl group, tolyl group, xylyl group, and other such aryl groups; and the benzyl group, phenethyl group, and other such aralkyl groups, with the methyl group being particularly favorable. The $R^3$ groups in the formula are the same or different divalent hydrocarbon groups or groups expressed by the formula:

—$R^6$—O—

Examples of the divalent hydrocarbon group of $R^3$ include the methylene group, ethylene group, propylene group, and other such alkylene groups; and the methylenephenylene group, ethylenephenylene group, and other such alkylenearylene groups. It is preferred that these $R^3$ groups be alkylene groups. a in the formula is 1 or 2, and preferably 1. b in the formula is an integer from 0 to 3, and preferably an integer from 0 to 2. m in the formula is 0 or 1. n in the formula is an integer from 0 to 2. p in the formula is 0 or 1. q in the formula is an integer from 0 to 7, and preferably 0 or 1. It is particularly preferred that the organosilicon compound of component (C) be an organosilicon compound in which X in the general formula given above is an isopropenyl group, Z is a carboxy group expressed by the formula —C(O)O—, p is 1, and m is 1, or more specifically, an organosilicon compound expressed by the general formula:

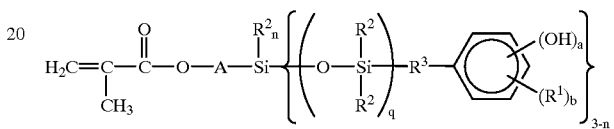

or an organosilicon compound in which Z in the general formula given above is an oxy group expressed by the formula —O—, p is 1, and q is 1, or more specifically, an organosilicon compound expressed by the general formula:

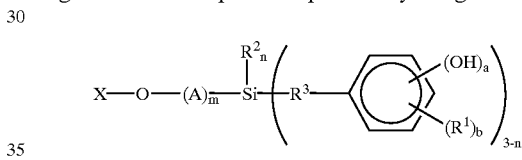

The following compounds of this organosilicon compound of components (C).

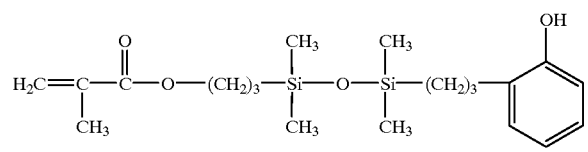

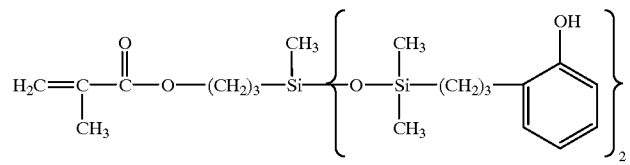

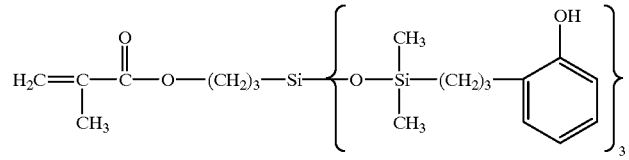

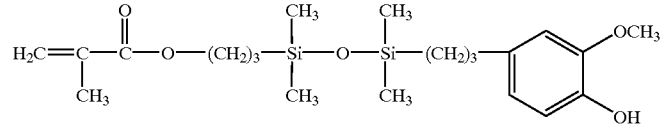

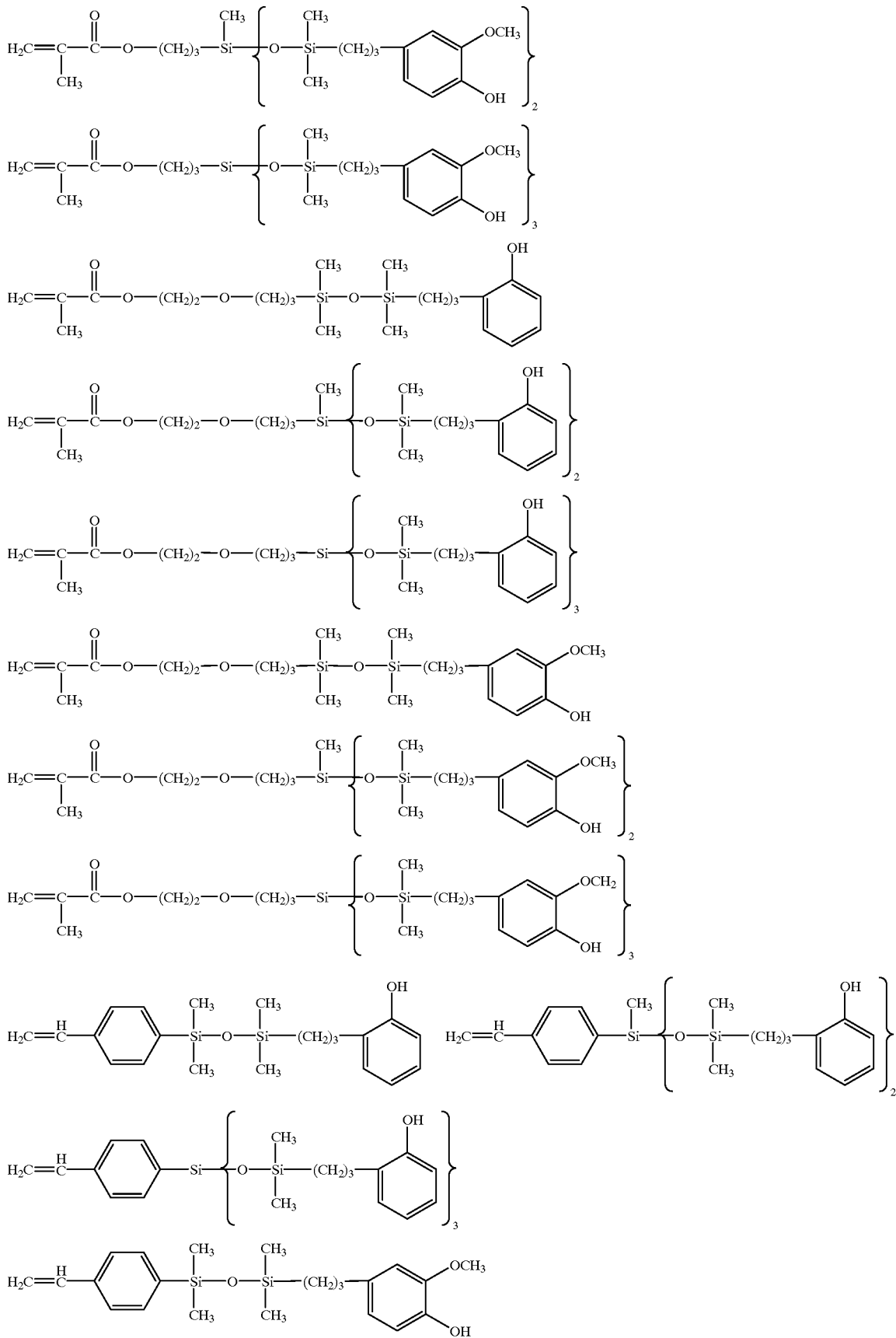

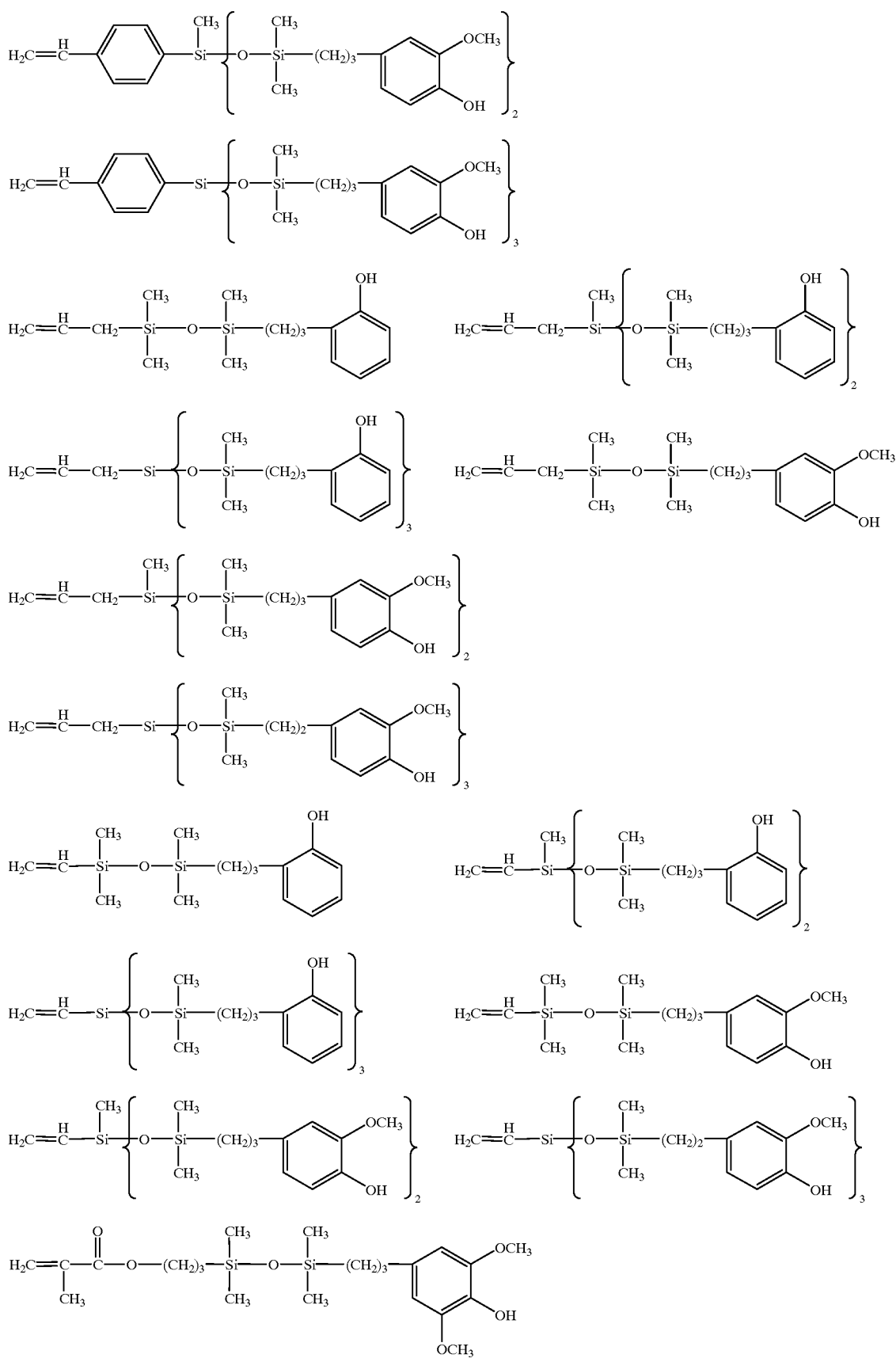

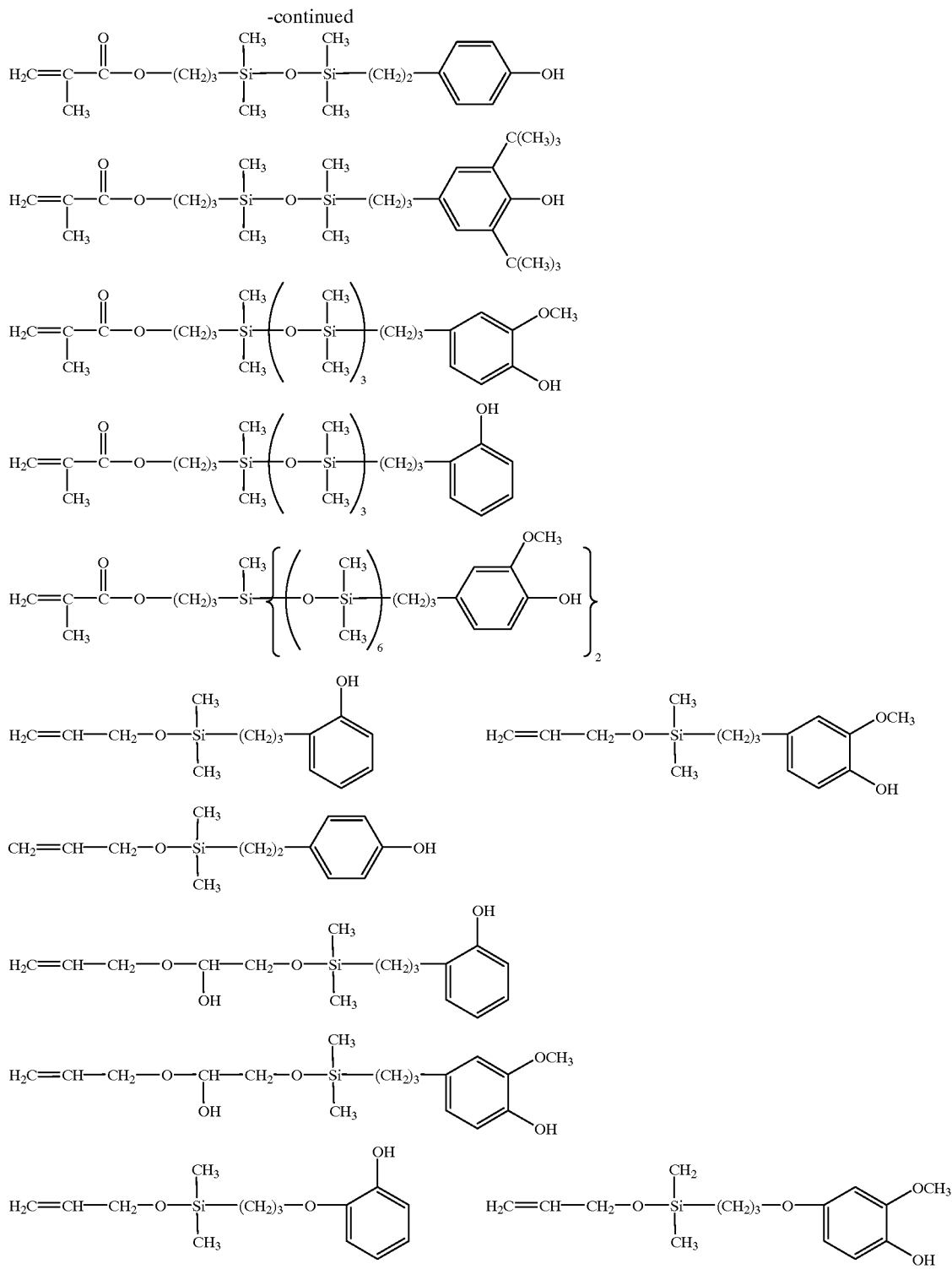

The amount of component (C) which is contained in this composition is between 0.1 and 50 weight parts, with 1 and 20 weight parts preferred, and between 1 and 10 weight parts, per 100 weight parts of component A particularly preferred Component (D) is a hydrosilylation reaction catalyst that serves to promote the curing of this composition. A conventional catalyst can be used as this component (D), specific examples of which include chloroplatinic acid, an alcohol solution of chloroplatinic acid, an olefin complex of platinum, a diketone complex of platinum, an acetyl acetate complex of platinum, a vinyl group-containing siloxane complex of platinum, and other platinum-based catalysts; a triphenylphosphine complex of rhodium and other rhodium-based catalysts; a tetrakis(triphenylphosphine) palladium complex and other palladium-based catalysts; compounds of ruthenium, iridium, iron, cobalt, manganese, zinc, lead, aluminum, nickel, and the like; and peroxides, azo compounds, and other radical generators. Of these, a platinum-based catalyst is preferred because it promotes a hydrosilylation reaction especially well. Two or more types of the above catalysts may also be used together as needed for this hydrosilylation reaction catalyst.

The amount of component (D) which is contained in this composition is an amount large enough to promote the curing of this composition, and when a platinum-based catalyst is used as component (D), it is preferred for the platinum metal in component (D) to be contained in this composition in an amount between 0.01 and 1000 ppm (weight units), with an amount between 0.1 to 500 ppm being particularly preferred, and an amount between 0.1 to 100 ppm being most preferred.

This composition is prepared by mixing the above-mentioned components (A) to (D). A hydrosilylation reaction inhibitor may also be added as an optional component for enhancing the storage stability of this composition. Examples of this hydrosilylation reaction inhibitor include triphenylphosphine and other phosphorus compounds, tributylamine, tetramethylethylenediamine, benzotriazole, and other nitrogen-containing compounds, sulfur-containing compounds, acetylene-based compounds, compounds having two or more alkenyl groups, compounds containing alkynyl groups, hydroperoxy compounds, maleic acid derivatives, and other such known compounds, with compounds having two or more alkynyl groups being preferred, and compounds having at least two alkynyl groups per molecule, compounds having an alkynyl group and an alcoholic hydroxyl group per molecule, 1,3-divinyl-1,1,3,3-tetramethyldisiloxane, and maleic diesters being particularly preferred.

There are no particular restrictions on the amount in which this hydrosilylation reaction inhibitor is contained in this composition, but the hydrosilylation reaction inhibition effect will be inadequate if this amount is too small, and curing will be far slower if the amount is too large, so it is preferable for this inhibitor to be contained in this composition in an amount between 0.1 and 50,000 ppm (weight units).

A known adhesion promoter can also be added to this composition as another optional component in order to improve adhesion with metal, glass, and other inorganic substances. A pigment can also be contained for coloring, a reinforcing filler to increase strength, a plasticizer to enhance melting under heating and to make the composition easier to work with, an additive for improving thermal conductivity, or a filler to increase electrical conductivity, for example.

The curable organosiloxane composition of the present invention cures quickly at room temperature or under heating and can be molded into a cured product in the form of a resin or in an elastomeric form such as a gel or rubber. A characteristic of the present invention is that epoxy resins, phenol resins, melamine resins, urea resins, polyurethane resins, polyimide resins, and other such thermosetting organic resins adhere well to this cured product, so it can be used favorably as a silicone rubber composition for compound molding, or as a silicone-type die bonding agent.

The organosilicon compound and curable organosiloxane composition of the present invention will now be described in further detail through working examples. The viscosity mentioned in these examples is the value measured at 25° C.

EXAMPLES

Reference Example 1

73.7 g of 1,1,3,3-tetramethyldisiloxane, 18 g of ice, 100 g of water, and 50 g of concentrated hydrochloric acid were added to a flask equipped with an agitator, a thermometer, a condenser, and a dropping funnel. 215.7 g of methacryloxypropyldimethylchlorosilane was added dropwise to the flask while the system was cooled in an ice bath so that the reaction temperature did not exceed 10° C. Upon completion of the dropping, the flask was allowed to stand so as to separate the aqueous layer, and the organic layer thus obtained was washed twice with water. This organic layer was then washed twice with a 5% aqueous solution of sodium hydrogencarbonate, and washed two more times with water. After the removal of the aqueous layer, sodium sulfate was added to the organic layer to dry it, after which the sodium sulfate was filtered off. 0.6 g of phenothiazine was then added to this product, and the system was distilled under reduced pressure, which yielded 198 g of a fraction of 71 to 80° C./1 mmHg. This fraction was analyzed by nuclear magnetic resonance (hereinafter referred to as NMR) and infrared spectroscopic analysis (hereinafter referred to as IR), which revealed it to be a disiloxane expressed by the following formula 1:

Formula 1

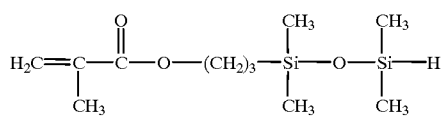

Working Example 1

28.66 g of the compound expressed by the following formula 2, 0.030 g of a polymerization inhibitor expressed by the following formula 3, and 17 μL of a toluene solution of a complex of chloroplatinic acid and 1,3-divinyltetramethyl-disiloxane (platinum metal concentration: 2 wt %) were added to a 100 mL three-necked flask to which a thermometer and a dropping funnel had been attached. The system was then heated to 80° C., and 4.02 g of the trisiloxane expressed by the following formula 7 was added dropwise. Upon completion of this dropping, the system was agitated for 40 minutes at 80° C., the reaction solution was analyzed by GLC and IR, and the reaction was concluded at the point when the signal representing the disiloxane in the raw material had disappeared according to GLC and the signal representing the silicon atom-bonded hydrogen atoms had disappeared according to IR. The unreacted compounds expressed by the following formulae (2 and 3) were distilled off from the reaction solution under heating and reduced pressure, which yielded 54.54 g of residue.

Formula 2:

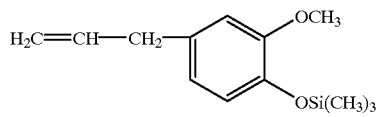

Formula 3:

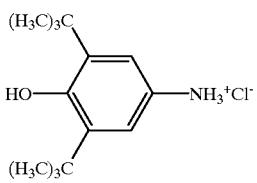

53.90 g of this residue, 45.0 g of methanol, 30.0 g of tetrahydrofuran, 1.24 g of diethylamine, and a rotator were then placed in a 200 mL four-necked flask to which a reflux condenser and a thermometer had been attached, and the system was heated to reflux for 2 hours at 60° C. The low-boiling matter was then distilled off, which yielded 46.73 g of residue. This was analyzed by NMR and IR, which revealed it to be a hydroxyphenyl group-containing methacrylic functional organosilicon compound expressed by the following formula 4. GLC revealed the purity of this organosilicon compound to be 93.9%.

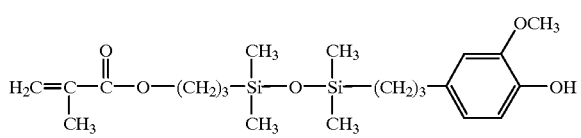

Reference Example 2

As noted above, 73.7 g of 1,1,3,3-tetramethyldisiloxane, 18 g of ice, 100 g of water, and 50 g of concentrated hydrochloric acid were placed in a 1 L flask equipped with an agitator, a thermometer, a cooling pipe, and a dropping funnel. 215.7 g (1 mol) of 3-methacryloxypropyldimethylchlorosilane was added dropwise to this flask while the system was cooled in an ice bath so that the reaction temperature would not exceed 10° C. Upon completion of this dropping, the flask was allowed to stand so as to separate the aqueous layer, and the organic layer thus obtained was washed twice with water. This organic layer was washed twice with a 5% sodium hydrogencarbonate aqueous solution, and then washed two more times with water. After the removal of the aqueous layer, sodium sulfate was added to the resulting organic layer to dry it, after which the sodium sulfate was filtered off. 0.6 g of phenothiazine was then added to this product, and the system was distilled under reduced pressure, which yielded 198 g of a fraction of 71 to 80° C./1 mmHg. This fraction was analyzed by nuclear magnetic resonance (hereinafter referred to as NMR) and infrared spectroscopic analysis (hereinafter referred to as IR), which revealed it to be a disiloxane expressed by the following formula.

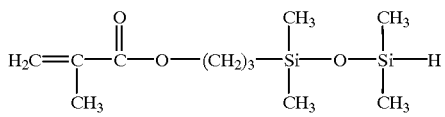

This disiloxane was analyzed by gas chromatography (hereinafter referred to as GLC), which revealed the purity to be 99%.

Reference Example 3

A rotor, 28.66 g of the compound expressed by the formula:

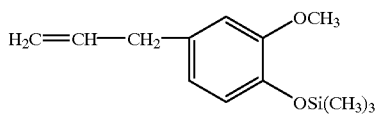

0.030 g of a polymerization inhibitor expressed by the formula:

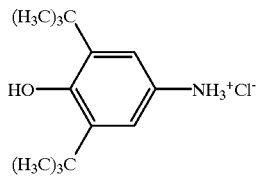

and 17 μL of a toluene solution of a complex prepared from chloroplatinic acid and 1,3-divinyltetramethyldisiloxane (platinum metal concentration: 2 wt %) were placed in a 100 mL three-necked flask to which a reflux condenser, a thermometer, and a dropping funnel had been attached. The system was then heated to 80° C., and 30.03 g of the disiloxane synthesized in Reference Example 2 was added dropwise. Upon completion of this dropping, the system was agitated for 40 minutes at 80° C., and the reaction solution was analyzed by GLC and IR, wherein GLC revealed that the signal representing the disiloxane in the raw material had disappeared, and IR that the signal representing the silicon atom-bonded hydrogen atoms had disappeared. The unreacted compounds were distilled off from the reaction solution under heating and reduced pressure, which yielded 54.54 g of residue.

53.90 g of this residue, 45.0 g of methanol, 30.0 g of tetrahydrofuran, 1.24 g of diethylamine, and a rotor were then placed in a 200 mL flask to which a reflux condenser and a thermometer had been attached, and the system was heated to reflux for 2 hours at 60° C. The low-boiling matter was then distilled off, which yielded 46.73 g of residue. This was analyzed by NMR and IR, which revealed it to be a phenol group-containing methacrylic functional organosilicon compound expressed by the formula:

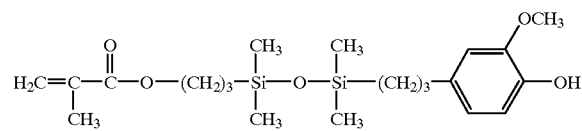

GLC revealed the purity of this organosilicon compound to be 93.9%.

Reference Example 4

A rotor, 6.19 g of the compound expressed by the formula:

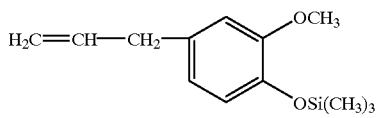

0.0048 g of a polymerization inhibitor expressed by the formula:

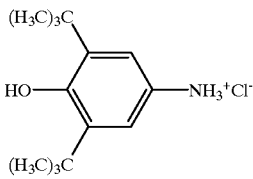

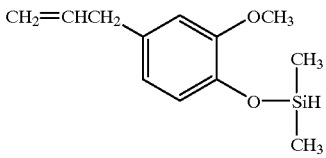

and 3 μL of a toluene solution of a platinum vinylsiloxane complex prepared from chloroplatinic acid and 1,3-divinyltetramethyldisiloxane (platinum metal concentration: 2 wt %) were placed in a 50 mL two-necked flask to which a thermometer and a dropping funnel had been attached. The system was then heated to 80° C., and 4.01 g of the trisiloxane expressed by the formula:

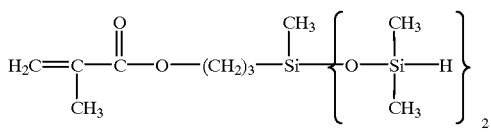

was added dropwise. Upon completion of this dropping, the system was agitated for 1 hour at 95° C., and the reaction solution was analyzed by GLC and IR, wherein GLC revealed that the signal representing the disiloxane in the raw material had disappeared, and IR that the signal representing the silicon atom-bonded hydrogen atoms had disappeared. It was concluded from this that the reaction had concluded, and the unreacted compounds were distilled off from the reaction solution under heating and reduced pressure. A reflux condenser was then attached, 6.00 g of methanol and 0.15 g of diethylaamine were added, and the system was heated to reflux for 1 hour at 56° C. The low-boiling matter was then distilled off, which yielded 7.69 g of residue. This was analyzed by NMR and IR, which revealed it to be a phenol group-containing methacrylic functional organosilicon compound expressed by the formula:

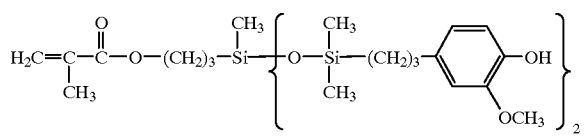

NMR revealed the purity of this organosilicon compound to be 88%.

Reference Example 5

100 g of toluene and 50 μL of a toluene solution of a platinum vinylsiloxane complex prepared from chloroplatinic acid and 1,3-divinyltetramethyldisiloxane (platinum metal concentration: 2 wt %) were placed in a 300 mL four-necked flask to which a reflux condenser, a thermometer, a dropping funnel, and an agitator had been attached. The system was then heated to 90° C., and 113.80 g of the organosilicon compound expressed by the formula:

was added dropwise. Upon completion of this dropping, the system was agitated for 3 hours at 100° C., and the reaction solution was analyzed by IR, which revealed that the reaction had concluded since the signal representing silicon atom-bonded hydrogen atoms had almost completely disappeared. The above reaction solution was poured into a 500 mL four-necked flask equipped with a reflux condenser, a thermometer, an agitator, to which 101 g of allyl alcohol, 40 g of tetrahydrofuran, and 20 mL of diethylamine were added, and the system was agitated for 14 hours at 90° C. Upon completion of this agitation, low-boiling matter was distilled off from the reaction solution under heating, which yielded 116.50 g of reaction product. This was analyzed by NMR and IR, which revealed it to be an organosilicon compound expressed by the formula:

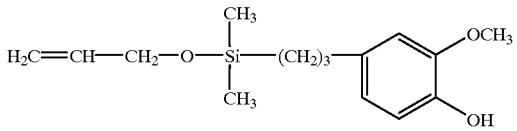

GLC revealed the purity of this organosilicon compound to be 93.4%.

Working Example 2

A curable organosiloxane composition was prepared by mixing 10.01 g of a dimethylvinylsiloxy group-capped dimethylpolysiloxane capped at both ends of the molecular chain and having a viscosity of 20000 mm$^2$/s, 0.3754 g of a trimethylsiloxy group-capped methylhydrogenpolysiloxane capped at both ends of the molecular chain and having a viscosity of 30 mm$^2$/s, 0.505 g of eugenol, 0.613 mg of phenylbutynol, and a complex of chloroplatinic acid and 1,3-divinyltetramethyldisiloxane in an amount such that the amount of platinum metal was 1 ppm with respect to the total amount of the composition.

This curable organosiloxane composition was cast onto a polyfluoroethylene plate and left in a 150° C. oven for 1 hour to cure, which yielded a silicone rubber sheet with a thickness of 10 mm. A polyfluoroethylene resin sheet with a hole in its center was placed on the surface of this silicone rubber sheet, and a commercially available curable epoxy resin was cast into this hole. A polyfluoroethylene resin sheet was then laid over this, and a weight placed on top. This test piece was put in a 150° C. oven and left for 1 hour, which cured the epoxy resin and produced a molded article in which the epoxy resin was integrated with the silicone rubber. The epoxy resin was then peeled away from this molded article, and the failure interface between the epoxy resin and the silicone rubber was observed visually, which revealed that this failure interface was cohesive failure, failing entirely in the silicone rubber layer. This revealed that the epoxy resin and the silicone rubber were securely bonded together.

Other than using a phenol/epoxy resin whose main components were an epoxy resin and a phenol resin instead of the commercially available epoxy resin used above, the adhesion of a phenol/epoxy resin to silicone rubber was examined in the same way as above. This phenol/epoxy resin was prepared by uniformly mixing 100 weight parts epoxy resin, 10 weight parts phenol resin, 5 weight parts 3-glycidoxy-propyltrimethoxysilane, and 20 weight parts imidazole-based curing agent. As a result, it was found that the failure interface was cohesive failure, failing entirely in the silicone rubber layer.

Working Example 3

A curable organosiloxane composition was prepared from 10.01 g of a dimethylvinylsiloxy group-capped dimethylpolysiloxane-diphenylsiloxane copolymer capped at both ends of the molecular chain and having a viscosity of 2000 mm$^2$/s, 0.1542 g of a trimethylsiloxy group-capped methylhydrogenpolysiloxane capped at both ends of the molecular chain and having a viscosity of 20 mm$^2$/s, 0.499 mg of phenylbutynol, and 0.413 g of phenol group-containing methacrylic functional organosilicon compound prepared in Reference Example 4.

Next, a complex of chloroplatinic acid and 1,3-divinyltetramethyldisiloxane was added to this composition in an amount such that the amount of platinum metal was 1 ppm with respect to the total amount of the composition, to prepare a curable organosiloxane composition. This curable organosiloxane composition was cast onto a polyfluoroethylene plate and left in a 150° C. oven for 1 hour to cure, which produced a silicone rubber sheet with a thickness of 10 mm. A polyfluoroethylene resin sheet with hole made in its center was placed on the surface of this silicone rubber sheet, and a commercially available curable epoxy resin was cast into this hole. A polyfluoroethylene resin sheet was then laid over this, and a weight placed on top. This test piece was placed in a 150° C. oven and left for 1 hour, which cured the epoxy resin and produced a molded article in which the epoxy resin was integrated with the silicone rubber. The epoxy resin was then peeled away from this molded article, and the failure interface between the epoxy resin and the silicone rubber was observed visually, which revealed that this failure interface was cohesive failure, failing entirely in the silicone rubber layer. This revealed that the epoxy resin and the silicone rubber were securely bonded together.

Other than using a phenol/epoxy resin whose main components were an epoxy resin and a phenol resin instead of the commercially available epoxy resin used above, the adhesion of a phenol/epoxy resin to silicone rubber was examined in the same way as above. This phenol/epoxy resin was prepared by uniformly mixing 100 weight parts epoxy resin, 10 weight parts phenol resin, 5 weight parts 3-glycidoxypropyltrimethoxysilane, and 20 weight parts imidazole-based curing agent. As a result, it was found that the failure interface was cohesive failure, failing entirely in the silicone rubber layer.

Working Example 4

An organopolysiloxane composition was prepared from 10.01 g of a dimethylvinylsiloxy group-capped dimethylpolysiloxane capped at both ends of the molecular chain and having a viscosity of 2000 mm$^2$/s, 1.00 g of fumed silica treated with hexamethyldisilazane, 0.27 g of a trimethylsiloxy group-capped methylhydrogenpolysiloxane capped at both ends of the molecular chain and having a viscosity of 20 mm$^2$/s, 1.014 g of the phenol group-containing organosilicon compound obtained in Reference Example 3, 2.81 mg of phenylbutynol, and a complex of chloroplatinic acid and 1,3-divinyltetramethyldisiloxane in an amount such that the amount of platinum metal was 1 ppm with respect to the total amount of the composition. This curable organosiloxane composition was cast onto a polyfluoroethylene plate and left in a 150° C. oven for 1 hour to cure, which produced a silicone rubber sheet with a thickness of 10 mm. A polyfluoroethylene resin sheet with a hole made in its center was placed on the surface of this silicone rubber sheet, and a commercially available curable epoxy resin was cast into this hole. A polyfluoroethylene resin sheet was then laid over this, and a weight placed on top. This test piece was put in a 150° C. oven and left for 1 hour, which cured the epoxy resin and produced a molded article in which the epoxy resin was integrated with the silicone rubber. The epoxy resin was then peeled away from this molded article, and the failure interface between the epoxy resin and the silicone rubber was observed visually, which revealed that this failure interface was cohesive failure, failing entirely in the silicone rubber layer. This revealed that the epoxy resin and the silicone rubber were securely bonded together.

Other than using a phenol/epoxy resin whose main components were an epoxy resin and a phenol resin instead of the commercially available epoxy resin used above, the adhesion of a phenol/epoxy resin to silicone rubber was examined in the same way as above. This phenol/epoxy resin was prepared by uniformly mixing 100 weight parts epoxy resin, 10 weight parts phenol resin, 5 weight parts 3-glycidoxypropyltrimethoxysilane, and 20 weight parts imidazole-based curing agent. As a result, it was found that the failure interface was cohesive failure, failing entirely in the silicone rubber layer.

Working Example 5

An organopolysiloxane composition was prepared by mixing 10.01 g of a dimethylvinylsiloxy group-capped dimethylpolysiloxane capped at both ends of the molecular chain and having a viscosity of 2000 mm$^2$/s, 0.2272 g of a trimethylsiloxy group-capped methylhydrogenpolysiloxane capped at both ends of the molecular chain and having a viscosity of 30 mm$^2$/s, 0.499 mg of phenylbutynol, 0.42 g of the organosilicon compound obtained in Reference Example 5, and a complex of chloroplatinic acid and 1,3-divinyltetramethyldisiloxane in an amount such that the amount of platinum metal was 1 ppm with respect to the total amount of the composition.

This curable organosiloxane composition was cast onto a polyfluoroethylene plate and left in a 150° C. oven for 1 hour to cure, which produced a silicone rubber sheet with a thickness of 10 mm. A polyfluoroethylene resin sheet with a hole made in its center was placed on the surface of this silicone rubber sheet, and a commercially available curable epoxy resin was cast into this hole. A polyfluoroethylene resin sheet was then laid over this, and a weight placed on top. This test piece was placed in a 150° C. oven and left for 1 hour, which cured the epoxy resin and produced a molded article in which the epoxy resin was integrated with the silicone rubber. The epoxy resin was then peeled away from this molded article, and the failure interface between the epoxy resin and the silicone rubber was observed visually, which revealed that this failure interface was cohesive failure, failing entirely in the silicone rubber layer. This revealed that the epoxy resin and the silicone rubber were securely bonded together.

Other than using a phenol/epoxy resin whose main components were an epoxy resin and a phenol resin instead of the commercially available epoxy resin used above, the adhesion of a phenol/epoxy resin to silicone rubber was examined in the same way as above. This phenol/epoxy resin was prepared by uniformly mixing 100 weight parts epoxy resin, 10 weight parts phenol resin, 5 weight parts 3-glycidoxypropyltrimethoxysilane, and 20 weight parts imidazole-based curing agent. As a result, it was found that the failure interface was cohesive failure, failing entirely in the silicone rubber layer.

Comparative Example 1

An organopolysiloxane composition was prepared from 10.04 g of a dimethylvinylsiloxy group-capped dimethylpolysiloxane capped at both ends of the molecular chain and having a viscosity of 2000 mm$^2$/s, 0.3620 g of a trimethylsiloxy group-capped methylhydrogenpolysiloxane capped at both ends of the molecular chain and having a viscosity of 30 mm$^2$/s, 0.594 g of the alicyclic epoxy functional compound expressed by the formula:

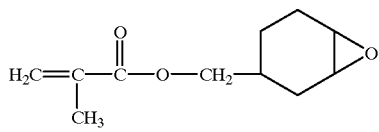

0.538 mg of phenylbutynol, and a complex of chloroplatinic acid and 1,3-divinyltetramethyldisiloxane in an amount such that the amount of platinum metal was 1 ppm with respect to the total amount of the composition.

This curable organosiloxane composition was cast onto a polyfluoroethylene plate and left in a 150° C. oven for 1 hour to cure, which produced a silicone rubber sheet with a thickness of 10 mm. A polyfluoroethylene resin sheet with a hole made in its center was placed on the surface of this silicone rubber sheet, and a commercially available curable epoxy resin was cast into this hole. A polyfluoroethylene resin sheet was then laid over this, and a weight placed on top. This test piece was placed in a 150° C. oven and left for 1 hour, which cured the epoxy resin and produced a molded article in which the epoxy resin was integrated with the silicone rubber. The epoxy resin was then peeled away from this molded article, and the failure interface between the epoxy resin and the silicone rubber was observed visually, which revealed that this failure interface was peeling at the interface between the silicone rubber layer and the epoxy resin layer, and 100% of the interface had peeled.

That which is claimed is:

1. A curable organosiloxane composition comprising:
   (A) an organopolysiloxane having at least two silicon atom-bonded alkenyl groups per molecule;
   (B) an organopolysiloxane having at least two silicon atom-bonded hydrogen atoms per molecule;
   (C) an organosilicon compound of the formula

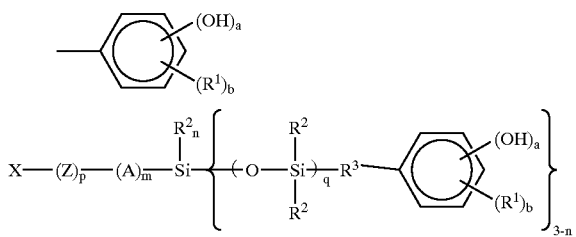

where X is an alkenyl group; Z is an oxy group expressed by the formula —O—, a carboxy group expressed by the formula —C(O)O—, or a phenylene group, A is a divalent hydrocarbon group, a group expressed by the formula

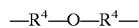

where the R$^4$ groups are divalent hydrocarbon groups, or a group expressed by the formula

where R$^5$ is a substituted or unsubstituted divalent hydrocarbon group, R$^1$ is an alkyl group or alkoxy group, the R$^2$ groups are monovalent hydrocarbon groups having no aliphatic unsaturated bonds, the R$^3$ groups are divalent hydrocarbon groups or groups expressed by the formula

where R$^6$ is a divalent hydrocarbon group, a is 1 or 2, b is 0 to 3, m is 0 or 1, n is 0 to 2, p is 0 or 1, and q is 0 to 7;
   (D) a hydrosilylation reaction catalyst.

2. A composition according to claim 1, wherein component (A) is selected from the group consisting of a trimethylsiloxy-endblocked methylvinylpolysiloxane, a trimethylsiloxy-endblocked dimethylsiloxane-methylvinylsiloxane copolymer, a trimethylsiloxy-endblocked diphenylsiloxane-methylvinylsiloxane copolymer, a dimethylvinylsiloxy-endblocked dimethylpolysiloxane, a dimethylvinylsiloxy-endblocked dimethylsiloxane-methylvinylsiloxane copolymer, a dimethylvinylsiloxyendblocked dimethylsiloxane-diphenylsiloxane copolymer, a cyclic methylvinylpolysiloxane, an organopolysiloxane comprising of siloxane units expressed by the formula SiO$_{4/2}$ and siloxane units expressed by the formula CH$_2$=CH(CH$_3$)$_2$SiO$_{1/2}$, and an organopolysiloxane comprising siloxane units expressed by the formula SiO$_{4/2}$, siloxane units expressed by the formula (CH$_3$)$_3$SiO$_{1/2}$, and siloxane units expressed by the formula CH$_2$=CH(CH$_3$)$_2$SiO$_{1/2}$.

3. A composition according to claim 1, wherein component (B) is selected from the group consisting of a trimethylsiloxy-endblocked methylhydrogenpolysiloxane, a trimethylsiloxy-endblocked dimethylsiloxane-methylhydrogensiloxane copolymer, a trimethylsiloxy-endblocked diphenylsiloxane-methylhydrogensiloxane copolymer, a dimethylhydrogensiloxy-endblocked dimethylsiloxane-methylhydrogensiloxane copolymer, a cyclic methylhydrogenpolysiloxane, an organopolysiloxane comprising siloxane units expressed by the formula SiO$_{4/2}$ and siloxane units expressed by the formula (CH$_3$)$_2$HSiO$_{1/2}$, and an organopolysiloxane comprising siloxane units expressed by the formula SiO$_{4/2}$, siloxane units expressed by the formula (CH$_3$)$_3$SiO$_{1/2}$, and siloxane units expressed by the formula (CH$_3$)$_2$HSiO$_{1/2}$.

4. A composition according to claim 2, wherein component (B) is selected from the group consisting of a trimethylsiloxy-endblocked methylhydrogenpolysiloxane, a trimethylsiloxy-endblocked dimethylsiloxane-methylhydrogensiloxane copolymer, a trimethylsiloxy-endblocked diphenylsiloxane-methylhydrogensiloxane copolymer, a dimethylhydrogensiloxy-endblocked dimethylsiloxane-methylhydrogensiloxane copolymer, a cyclic methylhydrogenpolysiloxane, an organopolysiloxane comprising siloxane units expressed by the formula SiO$_{4/2}$ and siloxane units expressed by the formula (CH$_3$)$_2$HSiO$_{1/2}$, and an organopolysiloxane comprising siloxane units expressed by the formula $SiO_{4/2}$, siloxane units expressed by the formula $(CH_3)_3SiO_{1/2}$, and siloxane units expressed by the formula $(CH_3)_2HSiO_{1/2}$.

5. A composition according to claim 1, wherein component (C) is an alkenyl group-containing phenol compound.

6. A composition according to claim 1, wherein component (C) is an organosilicon compound of the formula:

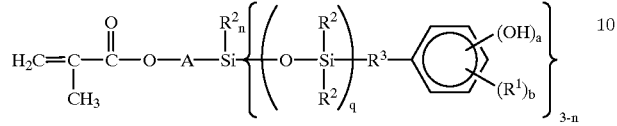

where A is a divalent hydrocarbon group, a group expressed by the formula:

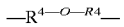

where the $R^4$ groups are divalent hydrocarbon groups, or a group expressed by the formula:

where $R^5$ is a substituted or unsubstituted divalent hydrocarbon group, $R^1$ is an alkyl group or alkoxy group, the $R^2$ groups are monovalent hydrocarbon groups having no aliphatic unsaturated bonds, the $R^3$ groups are divalent hydrocarbon groups or groups expressed by the formula:

where $R^6$ is a divalent hydrocarbon group, a is 1 or 2, b is an integer from 0 to 3, n is an integer from 0 to 2, and q is an integer from 0 to 7.

7. A composition according to claim 1, wherein component (C) is an organosilicon compound of the formula:

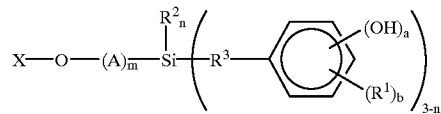

where X is an alkenyl group, A is a divalent hydrocarbon group, a group having the formula:

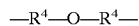

where the $R^4$ groups are divalent hydrocarbon groups, or a group expressed by the formula:

where $R^5$ is a substituted or unsubstituted divalent hydrocarbon group; $R^1$ is an alkyl group or alkoxy group, the $R^2$ groups are monovalent hydrocarbon groups having no aliphatic unsaturated bonds, the $R^3$ groups are divalent hydrocarbon groups or groups expressed by the formula:

where $R^6$ is a divalent hydrocarbon group, a is 1 or 2, b is an integer from 0 to 3, m is 0 or 1, and n is an integer from 0 to 2.

8. A curable organosiloxane composition according to claim 1, where in (C) is selected from the group consisting of

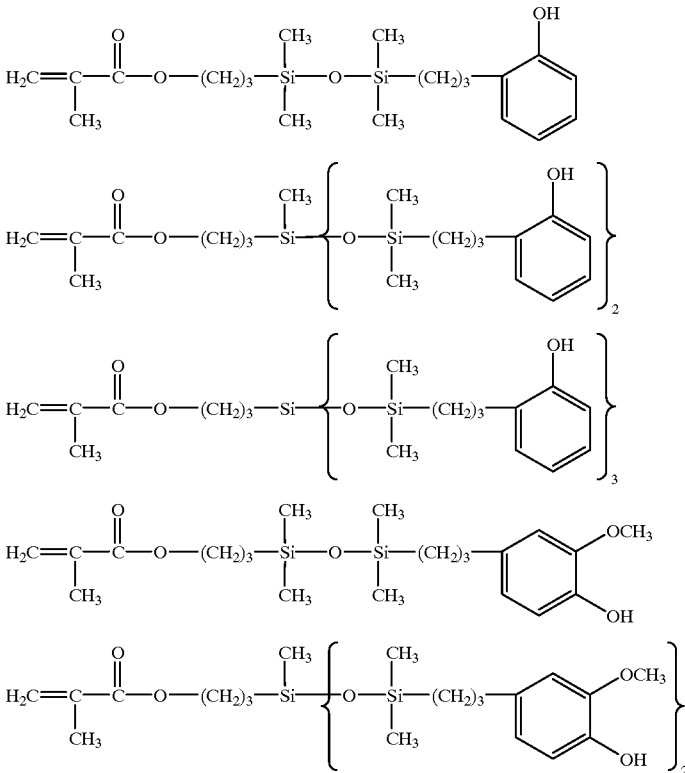

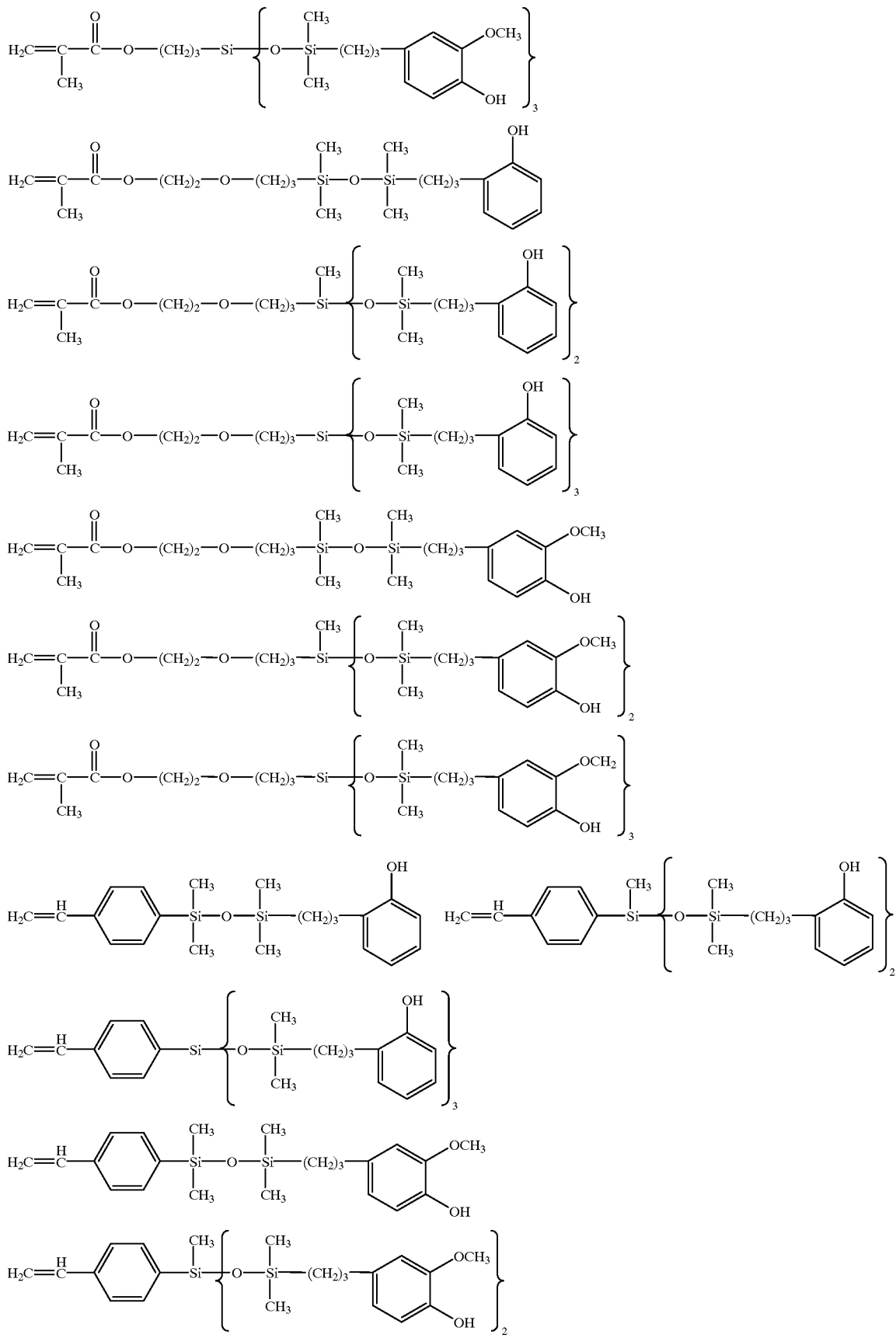

-continued
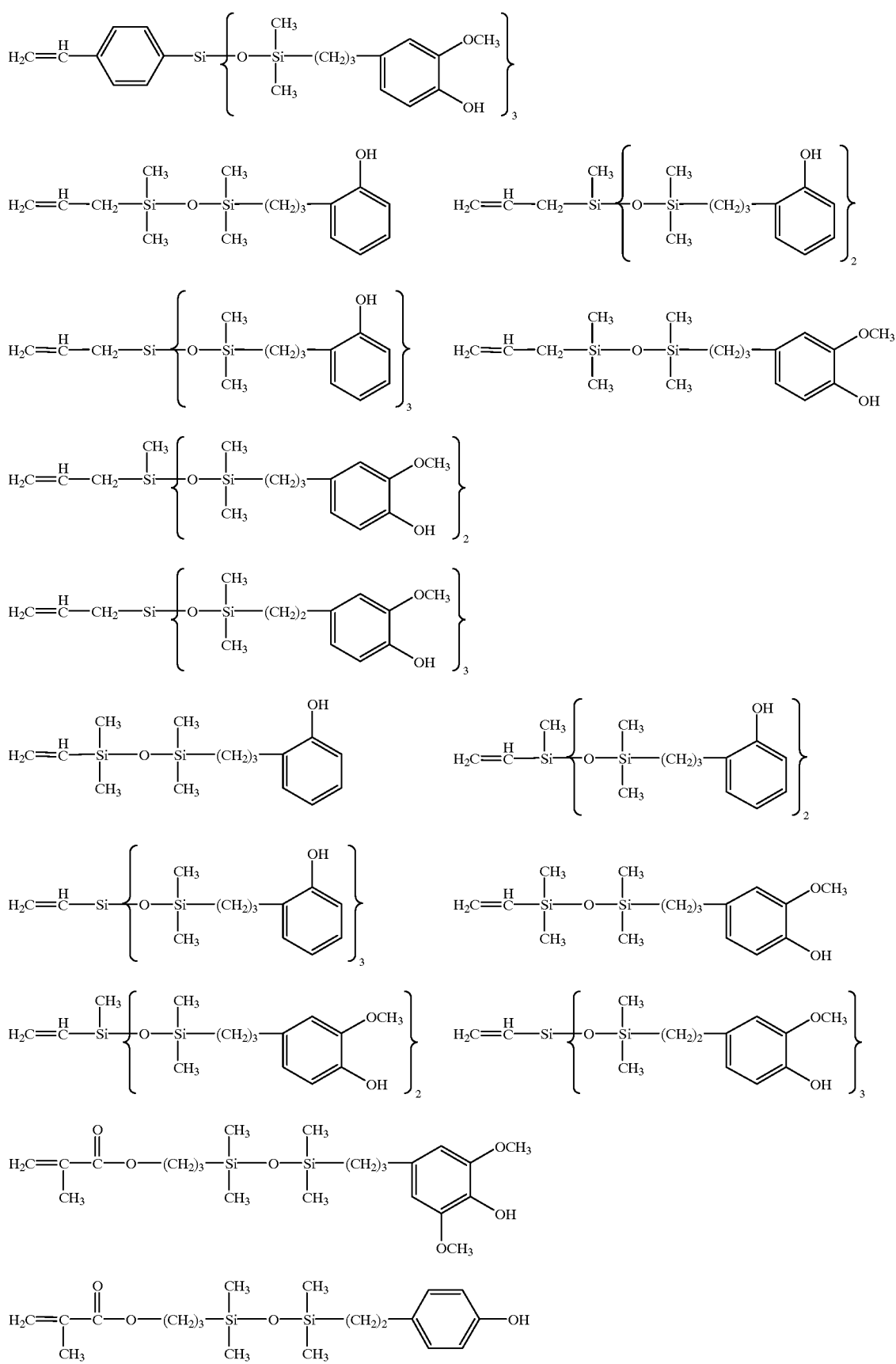

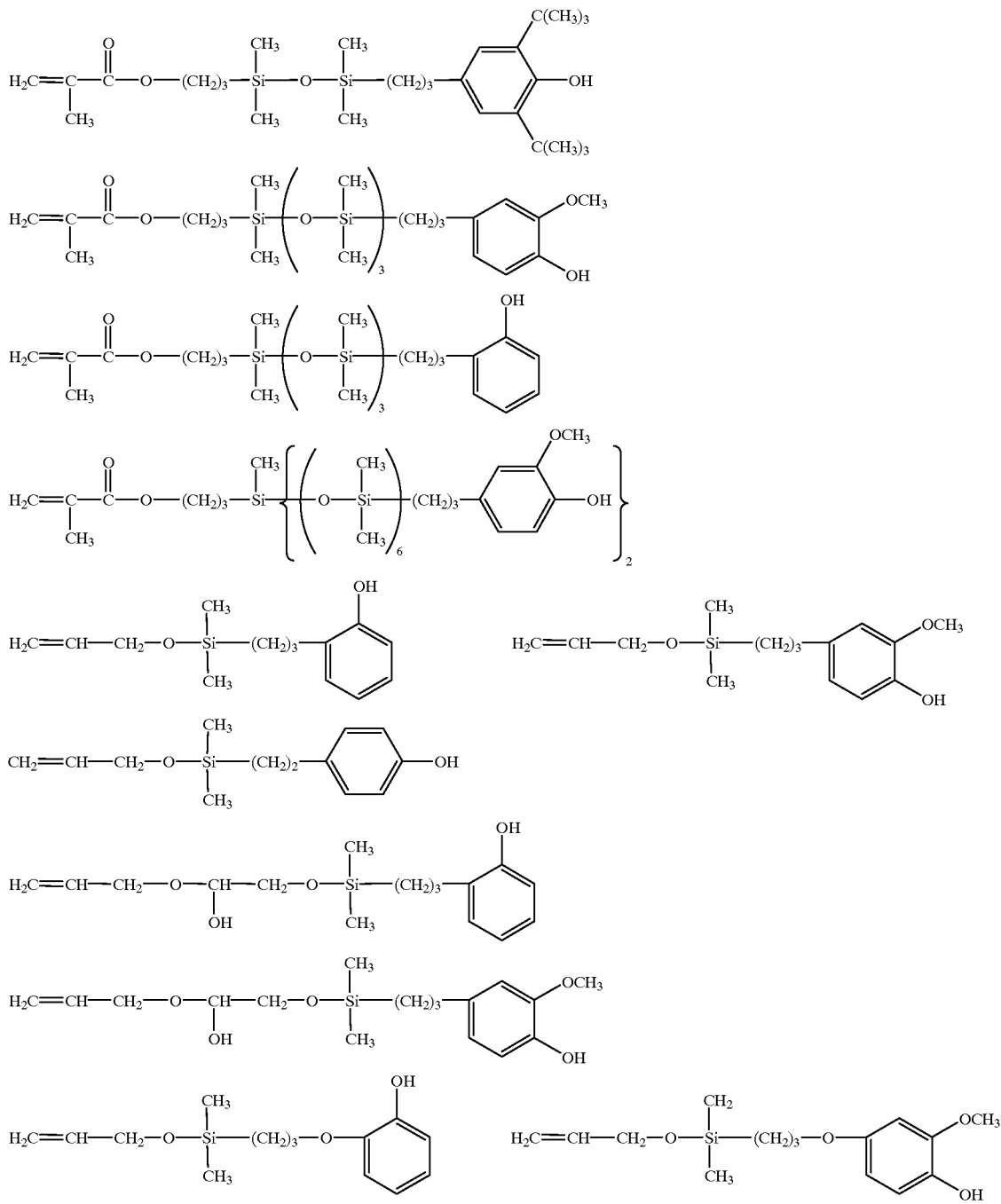

9. A curable organosiloxane composition according to claim 1, wherein (D) is selected from the group consisting of chloroplantinic acid, an alcohol solution of chloroplantinic acid, an olefin complex of platinum, a diketone complex of platinum, an acetyl acetate complex of platinum, and a vinyl group-containing siloxane complex of platinum.

10. A curable organosiloxane composition according to claim 1, wherein the composition further comprises at least one ingredient selected from the group consisting of a hydrosilylation reaction inhibitor, an adhesion promoter, a pigment, a reinforcing filler, a plasticizer, an additive for improving thermal conductivity, and a filler to increase electrical conductivity.

11. A composition according to claim 4, wherein component (C) is an organosilicon compound of the formula:

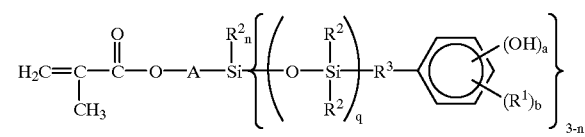

where A is a divalent hydrocarbon group, a group expressed by the formula:

—R⁴—O—R⁴— where the R⁴ groups are divalent hydrocarbon groups, or a group expressed by the formula:

—R⁵—O— where R⁵ is a substituted or unsubstituted divalent hydrocarbon group, R¹ is an alkyl group or alkoxy group, the R² groups are monovalent hydrocarbon groups having no aliphatic unsaturated bonds, the R³ groups are divalent hydrocarbon groups or groups expressed by the formula:

—R⁶—O— where R⁶ is a divalent hydrocarbon group, a is 1 or 2, b is an integer from 0 to 3, n is an integer from 0 to 2, and q is an integer from 0 to 7.

12. A curable organosiloxane composition according to claim 4, wherein component (C) is an organosilicon compound of the formula:

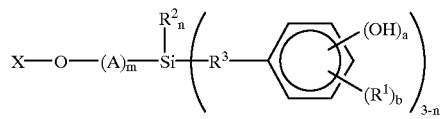

where X is an alkenyl group, A is a divalent hydrocarbon group, a group having the formula:

—R⁴—O—R⁴— where the R⁴ groups are divalent hydrocarbon groups, or a group expressed by the formula:

—R⁵—O— where R⁵ is a substituted or unsubstituted divalent hydrocarbon group; R¹ is an alkyl group or alkoxy group, the R² groups are monovalent hydrocarbon groups having no aliphatic unsaturated bonds, the R³ groups are divalent hydrocarbon groups or groups expressed by the formula:

—R⁶—O— where R⁶ is a divalent hydrocarbon group, a is 1 or 2, b is an integer from 0 to 3, m is 0 or 1, and n is an integer from 0 to 2.

13. A curable organosiloxane composition according to claim 4, where in (C) is selected from the group consisting of:

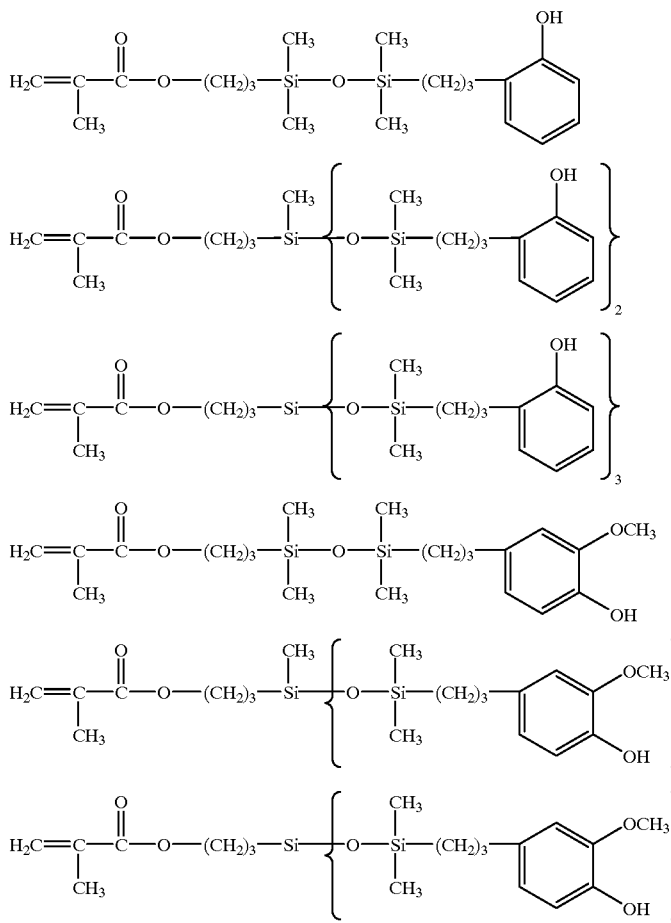

-continued
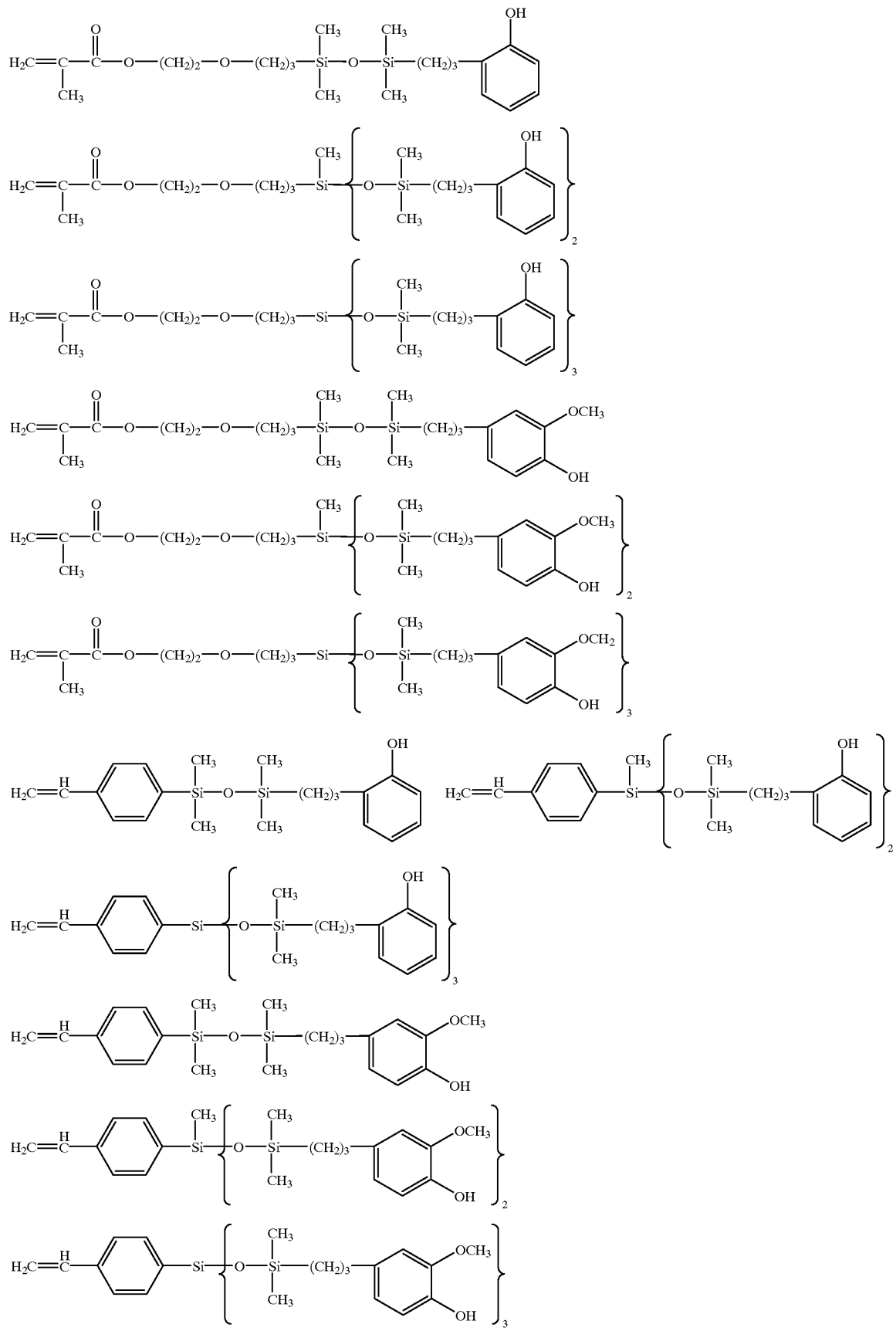

-continued
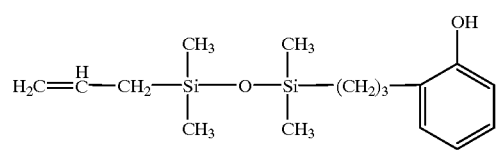
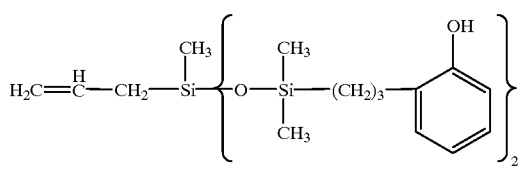
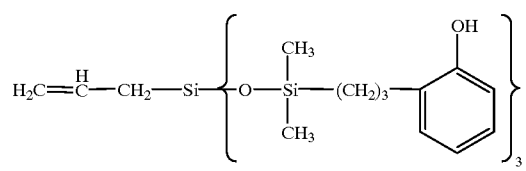
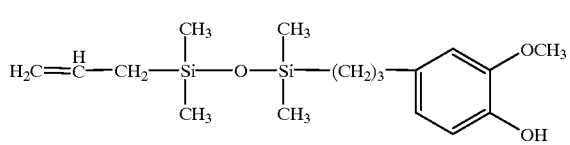
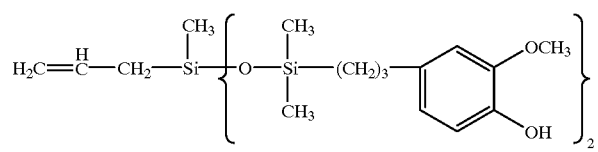
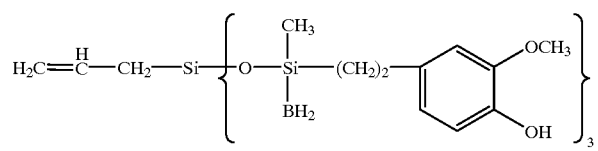
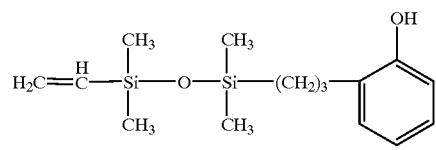
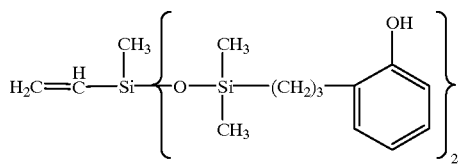
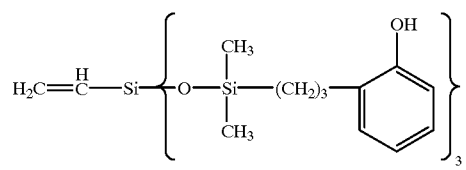
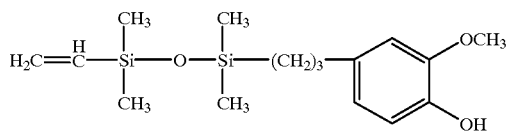
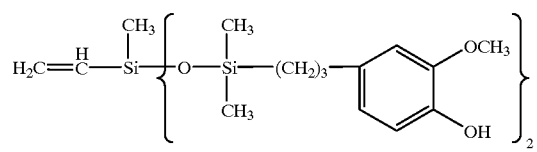
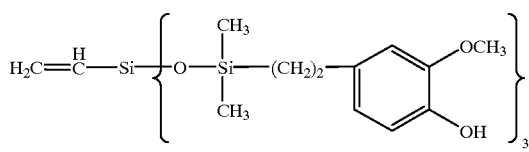
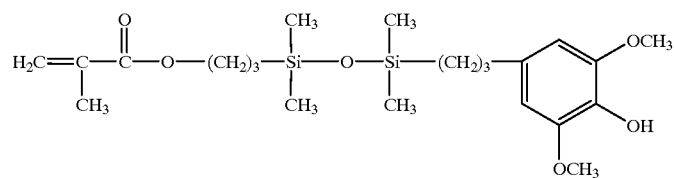
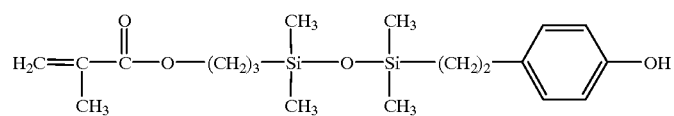
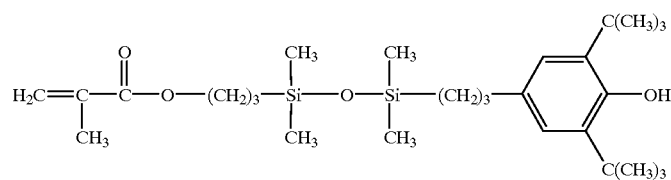

-continued

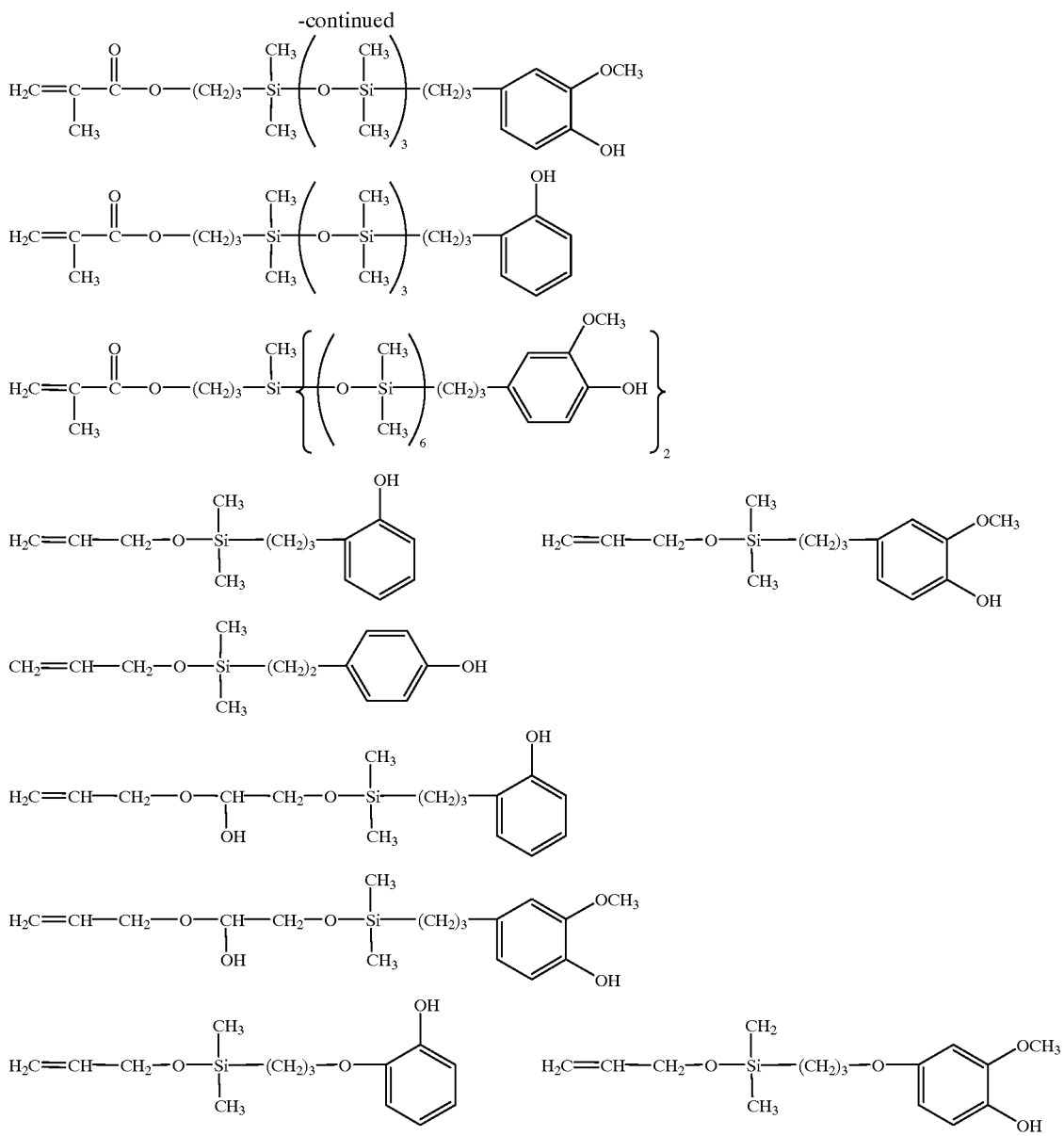

14. A curable organosiloxane composition according to claim 13, wherein (D) is selected from the group consisting of chloroplantinic acid, an alcohol solution of chloroplantinic acid, an olefin complex of platinum, a diketone complex of platinum, an acetyl acetate complex of platinum, and a vinyl group-containing siloxane complex of platinum.

15. A curable organosiloxane composition according to claim 14, wherein the composition further comprises at least one ingredient selected from the group consisting of a hydrosilylation reaction inhibitor, an adhesion promoter, a pigment, a reinforcing filler, a plasticizer, an additive for improving thermal conductivity, and a filler to increase electrical conductivity.

* * * * *